(12) United States Patent
Dawson

(10) Patent No.: US 10,384,237 B2
(45) Date of Patent: Aug. 20, 2019

(54) METHOD AND APPARATUS FOR DECONTAMINATING A MEDICAL INSTRUMENT

(71) Applicant: MEDISAFE UK LIMITED, Bishop's Stortford, Hertfordshire (GB)

(72) Inventor: Lawrence Ralph Dawson, Essex (GB)

(73) Assignee: Medisafe UK Limited, Bishops Stortford (GB)

( * ) Notice: Subject to any disclaimer, the term of this patent is extended or adjusted under 35 U.S.C. 154(b) by 754 days.

(21) Appl. No.: 14/425,363

(22) PCT Filed: Sep. 4, 2013

(86) PCT No.: PCT/GB2013/052319
§ 371 (c)(1),
(2) Date: Mar. 3, 2015

(87) PCT Pub. No.: WO2014/037720
PCT Pub. Date: Mar. 13, 2014

(65) Prior Publication Data
US 2015/0251224 A1 Sep. 10, 2015

Related U.S. Application Data

(60) Provisional application No. 61/696,422, filed on Sep. 4, 2012.

(30) Foreign Application Priority Data

Sep. 4, 2012 (GB) .................................. 1215782.2

(51) Int. Cl.
*B08B 3/04* (2006.01)
*B08B 9/00* (2006.01)
(Continued)

(52) U.S. Cl.
CPC ................ *B08B 3/04* (2013.01); *A61B 50/20* (2016.02); *A61B 50/22* (2016.02); *A61B 90/70* (2016.02);
(Continued)

(58) Field of Classification Search
None
See application file for complete search history.

(56) References Cited

U.S. PATENT DOCUMENTS 5,554,228 A 9/1996 Giordano et al. ............... 134/21
5,985,038 A * 11/1999 Dawson .................... B08B 3/12
134/1
2009/0158539 A1* 6/2009 Onishi ............... A61B 1/00057
15/104.066

FOREIGN PATENT DOCUMENTS

DE 10248460 4/2004 ............. A61M 1/00
EP 0822869 10/2003
(Continued)

OTHER PUBLICATIONS

DE10248460 English Translation accessed on Nov. 2017.*
(Continued)

*Primary Examiner* — Eric W Golightly
*Assistant Examiner* — Arlyn I Rivera-Cordero
(74) *Attorney, Agent, or Firm* — Kusner & Jaffe

(57) ABSTRACT

A method for decontaminating a medical instrument having parts that are movable relative to one another involves mounting the instrument in a decontaminating apparatus, and automatically manipulating the instrument to provide relative movement between two or more relatively movable parts of the instrument during an automated decontamination cycle of the decontaminating apparatus. The instrument may be a surgical instrument having an operating portion arranged to remotely control operation of a working portion in use. The method may involve engaging a part or parts of the operating portion to transmit motion thereto for creating the relative movement. An instrument carrier insertable in a decontaminating apparatus in use may be modified to incorporate an instrument manipulator.

14 Claims, 8 Drawing Sheets

(51) Int. Cl.
  *B08B 13/00* (2006.01)
  *A61B 50/22* (2016.01)
  *A61B 90/70* (2016.01)
  *A61B 50/20* (2016.01)
  *A61B 34/30* (2016.01)

(52) U.S. Cl.
  CPC ............. *B08B 9/00* (2013.01); *B08B 13/00* (2013.01); *A61B 34/30* (2016.02); *Y10T 29/49826* (2015.01)

(56) References Cited

FOREIGN PATENT DOCUMENTS

| | | | | |
|---|---|---|---|---|
| GB | 2397227 | 7/2004 | | |
| WO | WO 2012/148266 | 11/2012 | ............. | A61B 19/00 |
| WO | WO2012148266 | 11/2012 | | |

OTHER PUBLICATIONS

United Kingdom Office Action from corresponding GB 1505647.6, dated Feb. 28, 2017.
Search Report PCT, International Search Report; dated Oct. 28, 2013.
GB Search Report dated Jan. 22, 2013.

* cited by examiner

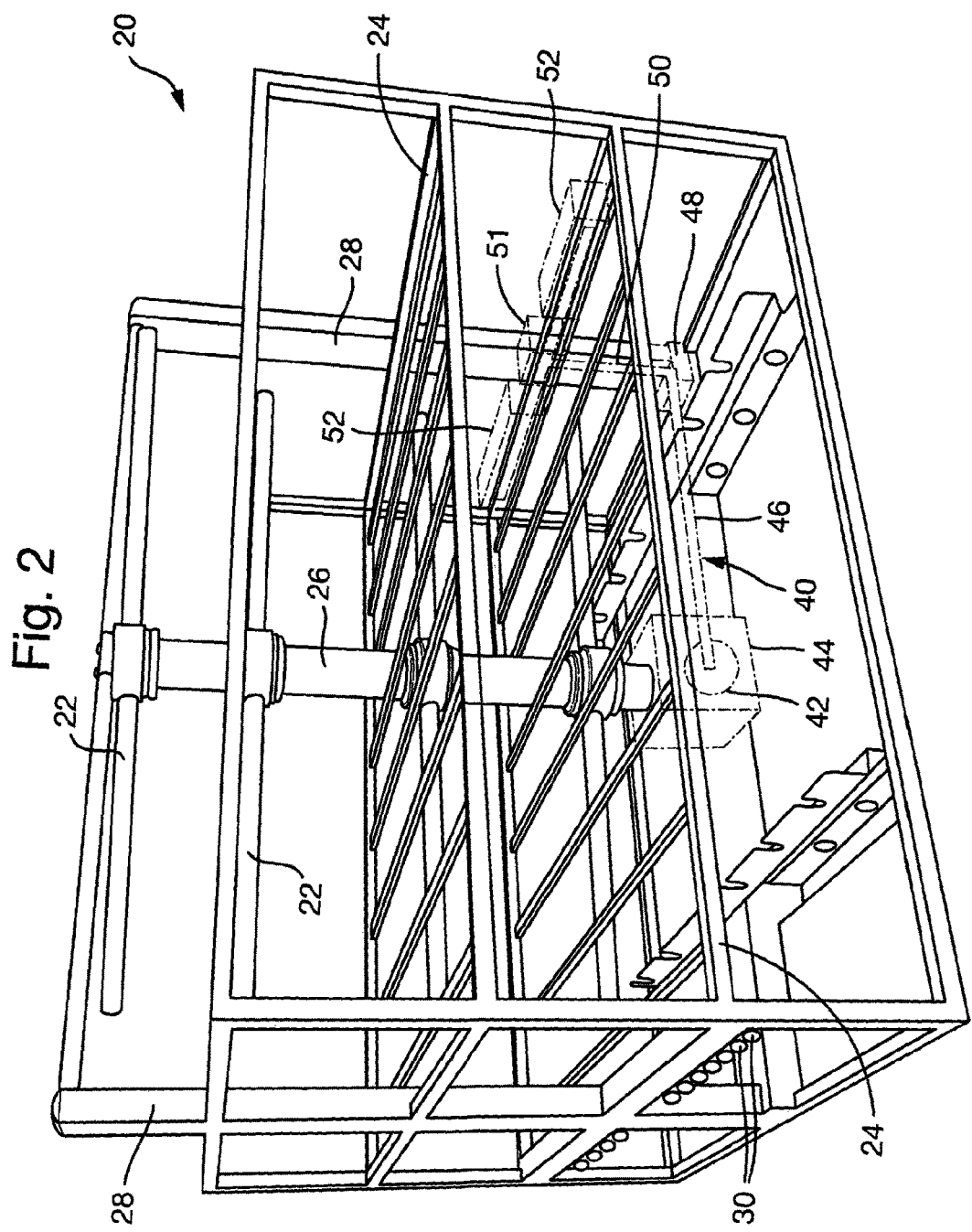

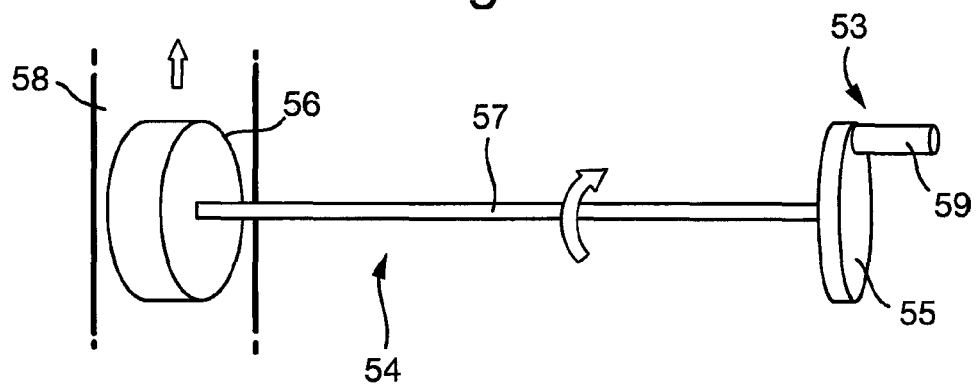
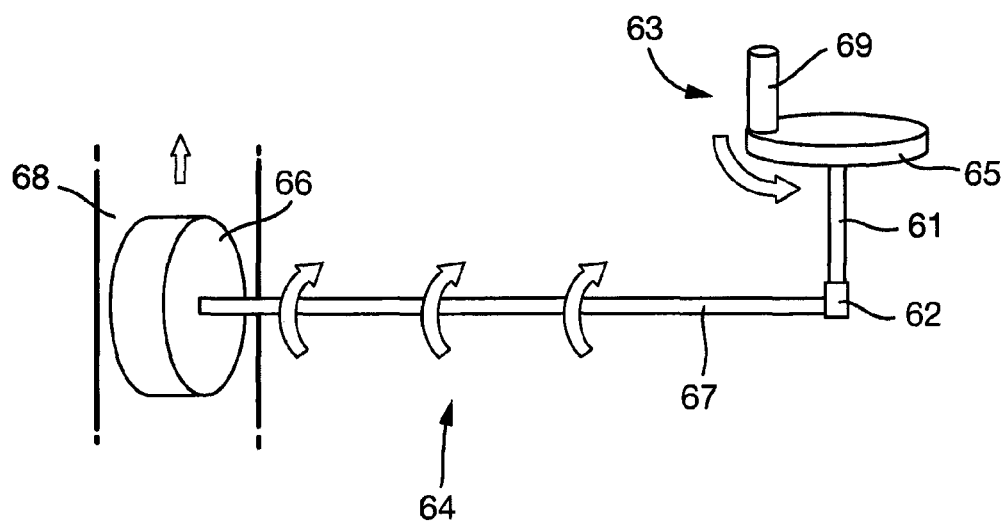

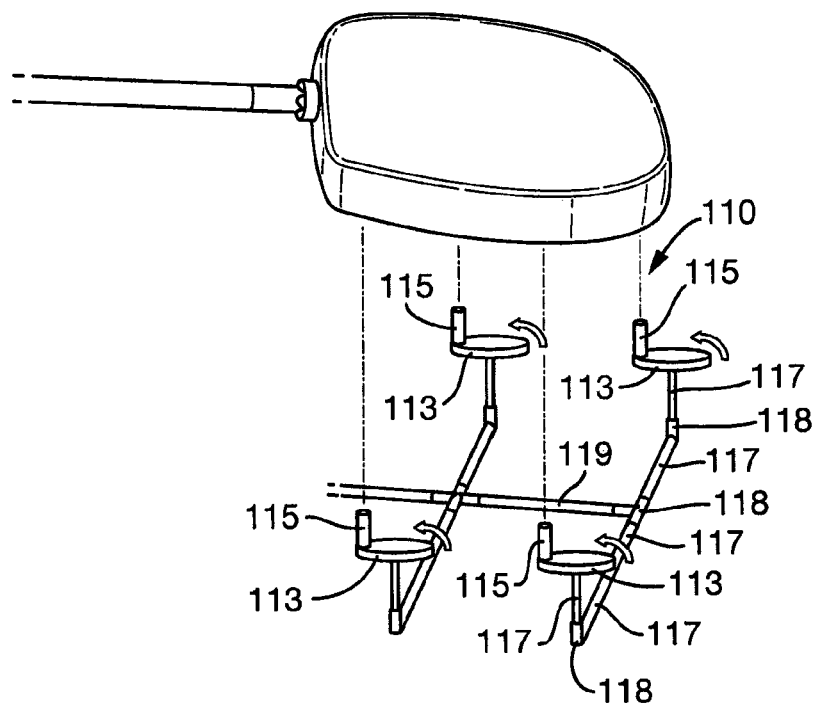
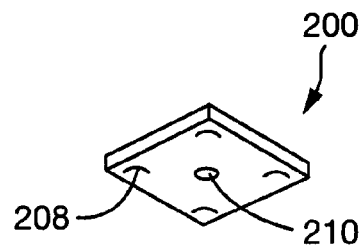

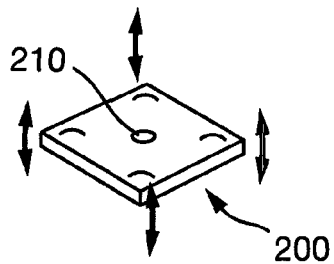
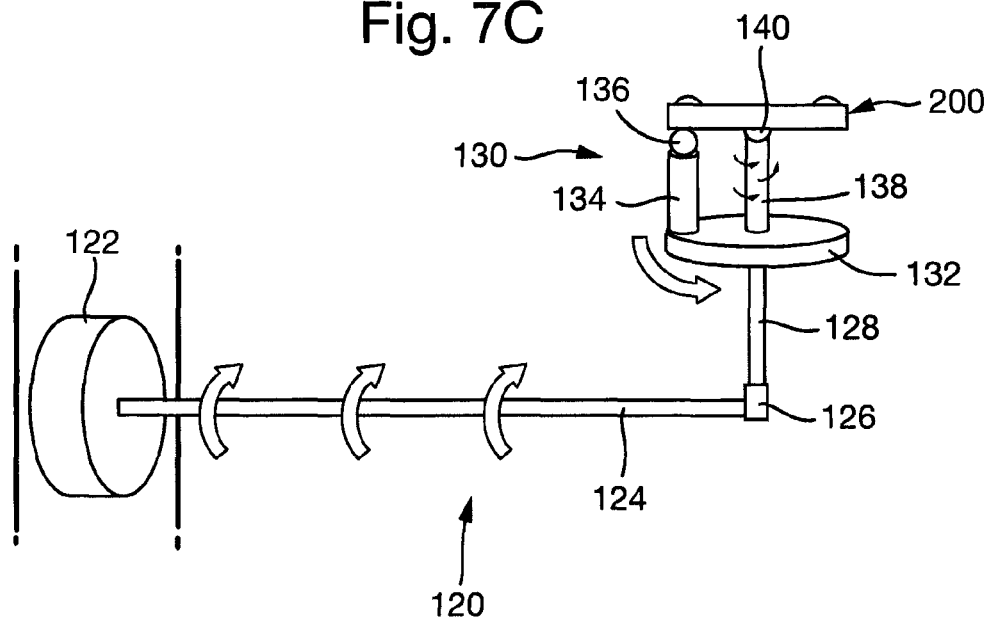

METHOD AND APPARATUS FOR DECONTAMINATING A MEDICAL INSTRUMENT

BACKGROUND

The present invention relates to a method and apparatus for decontaminating a medical instrument that has two or more parts that can move relative to one another in use. The invention is particularly, although not exclusively, applicable to the decontamination of surgical instruments. However the invention may also be used in the decontamination of other types of medical instrument, or other medical or surgical equipment or components having relatively movable parts. The present invention is applicable to the decontamination of medical instruments for use in any medical field, including dental and veterinary fields. The present invention relates to the automatic decontamination of medical instruments using a decontaminating apparatus.

Although the medical instruments may be constructed to be non-disposable, the present invention may also be used to decontaminate disposable instruments, which in many cases are too expensive to be disposed of after a single use. For example, the invention may be used to decontaminate so-called "reposable" instruments, which are limited to a certain number of uses e.g. 10 uses. Thus, the invention may be applied to non-disposable, disposable or semi-disposable or reposable instruments. Thus, the invention is broadly applicable to the decontamination of reusable medical instruments.

In decontaminating reusable instruments, it is important that all external surfaces of the instruments are thoroughly cleaned to remove any body fluids, proteins, tissue or bone fragments etc. Where an instrument includes an internal passageway, such as a tubular bore or cavity, the internal surfaces may also need to be cleaned. Cannulae and lumened instruments are examples of medical instruments having internal passageways to be cleaned. It is often desirable to disinfect instruments during the decontamination process to reduce the risk of transmitting infection between patients. Instruments may undergo sterilization as a final decontamination stage.

Decontamination may involve forcing pressurised fluid over the instruments to achieve cleaning. Disinfection may also be carried out in this way using fluid at an elevated temperature. The fluid may be water or may be a decontaminating fluid including one or more decontaminating agents. This so-called "deluge decontamination" is typically carried out in large deluge washer machines which spray fluid over the instruments in a similar manner to a dishwasher machine. Medisafe UK Limited's Niagara® range washers, e.g. the Niagara® Express, are examples of deluge decontamination systems. The machines may include flushing attachments to which cannulated instruments may be attached to permit decontamination of internal surfaces. One example of such an attachment is found in EP 0822869A1 entitled "Method and Apparatus for Cleaning Hollow Elements" filed on 19 Apr. 1996, with priority date of 24 Apr. 1995. The attachment described in this earlier document is arranged to provide a continuous pulsed flow of fluid to the interior of an instrument.

Alternatively or additionally, decontamination of medical instruments may involve the use of ultrasonic waves. In an ultrasonic decontamination process, the instrument is immersed in a bath of decontamination fluid. Ultrasonic transducers are used to excite fluid in the bath, causing ultrasonic waves to propagate through the fluid. The ultrasonic waves cause small, high pressure bubbles to form and collapse in the fluid at high frequency. This "cavitation" effect gives rise to pressure waves in the fluid, which acts to "scrub" the surfaces of the immersed instrument. In this way, debris attached to the surfaces of the instrument may be loosened. Fluid may be supplied to internal surfaces of the instruments during ultrasonic cleaning. Instruments may also be subjected to soaking in which they are immersed in fluid e.g. provided in an ultrasonic reservoir, but without the application of ultrasonic waves.

Ultrasonic decontamination may be carried out alone, or in combination with deluge decontamination. Deluge decontamination may be used to help flush debris dislodged by the ultrasonic decontamination from the surfaces of the instrument. Combined ultrasonic and deluge decontaminating washers are known. Examples include Medisafe UK Limited's Niagara® SI Ultrasonic® and Niagara®, SI PCF® machines. These machines include an ultrasonic reservoir situated in the base of a decontamination chamber, with deluge sprayers arranged above the reservoir. Instruments are inserted into the chamber at various levels. This may be achieved by placing the instruments directly on a carrier of the machine, or by first placing them in baskets which then placed on the carrier. The lowermost instruments may be immersed in the ultrasonic reservoir to enable ultrasonic decontamination to be carried out. This may be achieved by lowering the carrier appropriately and/or filling the ultrasonic reservoir with fluid to cover the instruments. The bath may or may not then be drained and/or the deluge sprayers operated. Operation of the deluge sprayers may provide deluge decontamination of those instruments situated in the upper parts of the decontamination chamber, and in some cases, the ultrasonically decontaminated instruments in the reservoir if drained. In other situations, decontamination may involve ultrasonic decontamination without deluge decontamination. Examples of such ultrasonic decontamination machines include Medisafe UK Limited's Sonic Irrigator® range e.g. the Sonic Irrigator® SA® and Sonic Irrigator® PCF®.

In general decontamination may include any or all of deluge decontamination, which may include pre wash, wash and rinsing stages, ultrasonic decontamination, soaking, disinfection, and sterilization.

Certain medical instruments include parts that are moved relative to one another in use e.g. when the instrument is manipulated or actuated. For example, an instrument may have a working portion having parts that are movable relative to one another to change a configuration thereof in use, or which working portion includes one or more parts that are moved relative to another part of the instrument e.g. to articulate or otherwise move the working portion. Decontaminating instruments of this type presents particular challenges to achieve adequate decontamination of all surfaces of the instruments given that relative movement of parts of the instrument will expose different surface to contaminants in use.

These issues may be encountered with any instrument having relatively movable parts, ranging from articulated instruments of a simple forceps or scissor-like form to more complex instruments which are increasingly used in surgery. Such complex instruments may be used e.g. in laparoscopic or minimally invasive procedures, and/or robot assisted procedures. A "complex" surgical instrument typically includes a working portion whose manipulation can be remotely controlled via an operating portion remote from the working portion. In many arrangements an operating portion is provided at a proximal end of an instrument, which instrument has a working portion or working end at a distal end. Manipulation of the working portion may, for example, involve relative movement between a part of the working portion and another part of the instrument to result in articulation of the working portion, or between parts of the working portion to provide actuation thereof e.g. to provide a grasping or cutting action. Some complex surgical instruments include a working portion comprising an end effector at the distal end of the instrument connected via a "wrist" to a shaft, providing various degrees of freedom of the end effector.

Control of the operating portion may be achieved directly by the surgeon manually manipulating an operating interface or one or more handles of a handle portion of the operating portion, or by coupling an operating interface of the operating portion to a robotic arm, which is controlled by a surgeon e.g. using a computer or movable input device such as a joystick. An operating portion may be connected via an operation transmission arrangement to the working portion for communicating an operation indicated at the operating portion. The operation transmission arrangement might comprise cables or a rod etc.

It will be appreciated that in addition to relative movement between parts of such instruments at the working end or portion, in remotely operated instruments there is typically also relative movement between parts of the operating portion and operation transmission arrangement involved in manipulating the instrument in use. Ensuring that all surfaces that may be exposed during manipulation, including those of the operating portion and operation transmission arrangement are adequately decontaminated presents further challenges.

SUMMARY

Accordingly, the Applicant has identified a need for an improved method and apparatus for automatically decontaminating medical instruments having parts that are movable relative to one another in use.

In accordance with a first aspect of the present invention there is provided;

a method for decontaminating a medical instrument having parts that are movable relative to one another; the method comprising:

mounting the instrument in a decontaminating apparatus, and automatically manipulating the instrument to provide relative movement between two or more relatively movable parts of the instrument during an automated decontamination cycle of the decontaminating apparatus.

In accordance with a second aspect of the invention there is provided an apparatus for decontaminating a medical instrument; the decontaminating apparatus comprising:

means for automatically manipulating a medical instrument of the type having parts that are movable relative to one another when mounted in the apparatus in use to provide relative movement between two or more relatively movable parts of the instrument during an automated decontamination cycle of the decontaminating apparatus.

The means for automatically manipulating a medical instrument when mounted in the apparatus in use to provide relative movement between two or more relatively movable parts of the instrument during an automated decontamination cycle of the decontaminating apparatus may be referred to herein for brevity as the "instrument manipulation means" or "automatic instrument manipulation means". The invention in accordance with one aspect ma) include any of the features or steps described in respect of any other aspect if not mutually inconsistent.

For the avoidance of doubt, it will be appreciated that the apparatus of the present invention in any of its embodiments may comprise means for carrying out any of the steps described by reference to the method aspects in any of their embodiments, and the method of the present invention in any of its embodiments may comprise carrying out any of the steps that the apparatus of any of its embodiments is arranged to perform if not explicitly stated herein. The means for automatically manipulating instruments may perform such a step when driven in use. The apparatus may comprise driving means for driving the manipulation means as discussed below.

The present invention also extends to a system comprising the apparatus in accordance with the invention of any of its aspects or embodiments in combination with a medical instrument to be decontaminated. The medical instrument may be mounted in the apparatus in a manner such that the means for automatically manipulating a medical instrument will manipulate the instrument in use to provide relative movement between two or more relatively movable parts of the instrument during an automated decontamination cycle of the decontaminating apparatus.

The present invention extends to a method of using the apparatus of any of the embodiments or aspects described herein, the method comprising mounting a medical instrument having parts that are movable relative to one another in the decontaminating apparatus in a manner such that the means for automatically manipulating a medical instrument manipulates the instrument to provide relative movement between two or more relatively movable parts of the instrument during an automated decontamination cycle of the decontaminating apparatus.

In embodiments of the invention the method of the present invention may use the decontaminating apparatus in accordance with any of the aspects or embodiments of the invention described herein. Preferably therefore the decontaminating apparatus used in accordance with the method of the invention in any of its embodiments comprises means for automatically manipulating a medical instrument mounted in the apparatus of the type having parts that are movable relative to one another to provide relative movement between two or more relatively movable parts of the instrument during an automated decontamination cycle of the decontaminating apparatus, and the method comprises automatically manipulating the instrument using such means. The method may comprise mounting an instrument in the apparatus in a manner such that the instrument manipulation means manipulates the instrument to provide the relative movement between two or more relatively movable parts thereof during the automated decontamination cycle.

Thus, in accordance with the invention, a method and apparatus are provided for decontaminating a medical instrument having relatively movable parts. The parts of the instrument are movable relative to one another in use. The method involves automatically manipulating the instrument during an automated decontamination cycle of a decontaminating apparatus so as to provide relative motion between two or more relatively movable parts of the instrument, and the apparatus comprises means for carrying out such a step.

It will be appreciated that the instrument is of a type that comprises two or more relatively movable parts. Where the instrument includes more than two relatively movable parts, the method may involve providing relative movement between two or more of the relatively movable parts, and the apparatus may be configured to provide relative movement between two or more of the parts. Thus it is envisaged that relative movement may be provided between any two or more of the relatively movable parts, and relative movement may be provided between less than all or all of the relatively movable parts of an instrument.

The relative movement between two or more parts of an instrument provided in accordance with the invention involves movement of at least one part of the instrument, and may involve movement of two or more parts. The relative movement between parts may involve movement of one or more, or each of the parts in question e.g. of a set of parts between which relative movement is provided. The relative movement may involve the relative movement between parts from a first relative position to a second relative position. The movement may be a continual movement in one direction, or between first and second given relative positions. The relative movement might be a reciprocating movement. The relative movement may involve a relative rotational movement or translational movement or combinations thereof.

In this manner, more thorough decontamination of the instrument may be achieved, as different surfaces of the instrument may be exposed for decontamination as the relative positions of parts of the instrument are changed during the decontamination cycle. It will be appreciated that the present invention involves providing relative movement between relatively movable parts of an instrument rather than agitation or other movement of the instrument as a whole. In preferred embodiments the instrument as a whole remains stationary while the relative movement is provided between parts thereof, although the movement of the instrument as a whole in addition to providing relative movement between parts is not excluded. The relative movement that is provided may, for example, result in an actuation e.g. articulation of a working portion of the instrument and/or an operating portion thereof to expose different surfaces during the decontamination process. In embodiments of the invention in any of its aspects at least one part, and preferably a plurality of parts of the instrument is/are stationary during the relative movement of the two or more parts in accordance with the invention.

The instrument manipulation that provides the relative movement between parts of an instrument takes place automatically during an automated cycle of a decontaminating apparatus. The automatic instrument manipulation is caused to occur between the start and the end of the cycle, and thus the automatic instrument manipulation means is operable between the start and the end of the cycle. It may occur at any point or points in the cycle, and may occur at a plurality of different times in the automated cycle. For example, automatic manipulation may occur intermittently, and may be pulsed on and off. The most appropriate point or points of the cycle at which to apply the instrument manipulation will depend upon the particular instrument to be decontaminated.

The decontamination cycle, and in embodiments the decontamination stages, may involve any one or ones of deluge decontamination, ultrasonic decontamination, soaking, internal flushing, disinfection, rinsing or sterilisation. Soaking involves immersion of instruments in decontaminating fluid. The instruments may be located in a reservoir of the apparatus for this stage. This may be an ultrasonic reservoir where the apparatus is capable of providing ultrasonic decontamination, without the application of ultrasonic waves i.e. without operating ultrasonic transducers associated with the reservoir for applying ultrasonic waves to fluid located therein. Internal flushing may be carried out at the same time as either deluge or ultrasonic decontamination stages or indeed any other stage.

Automatic manipulation may or may not occur simultaneously with any type of decontamination e.g. a deluge or ultrasonic decontamination stage of the cycle. The manipulation may or may not occur while decontaminating fluid is being delivered to or contacts the internal and/or external surfaces of the instrument and/or during the application of ultrasonic waves to a fluid in which the instrument is immersed. For example, manipulation might occur between stages of the cycle.

In preferred embodiments, however, the automatic instrument manipulation takes place simultaneously with decontaminating fluid contacting internal and/or external surfaces of the instrument. This may be while fluid is delivered to the external surfaces e.g. in deluge decontamination, or the internal surfaces in internal flushing, and/or while the instrument is immersed in fluid e.g. in a soaking stage with or without the application of ultrasonic waves. In some preferred embodiments automatic instrument manipulation takes place at least while the instrument being manipulated is immersed in decontaminating fluid. The fluid may be in an reservoir, which may be an ultrasonic reservoir. Ultrasonic waves may or may not be applied to the fluid in the reservoir while automatic manipulation is carried out. It has been found that movement of parts of instruments during ultrasonic cleaning may interfere with the development of ultrasonic waves. In general therefore, preferably the method comprises carrying out automatic manipulation of the instrument without simultaneously carrying out ultrasonic decontamination of the instrument, i.e. without immersing the instrument in a reservoir of fluid and applying ultrasonic waves thereto.

Of course, depending upon construction of the apparatus, different types of decontaminating means may be operated simultaneously, and the apparatus may be arranged to provide different types of decontamination in different regions thereof. For example, deluge decontamination means may be operated for providing deluge decontamination of instruments in a deluge decontaminating region at the same time as other instruments are immersed in fluid in a reservoir below the deluge decontaminating region with or without the application of ultrasonic waves for providing ultrasonic decontamination of instruments therein. Thus, a particular decontaminating means may be operated without all instruments being subjected to that type of decontamination, and different instruments may undergo different types of decontamination at the same time.

In some preferred embodiments, instrument manipulation occurs at least during operation of deluge decontamination means of the apparatus. The instrument being manipulated may or may not then be subjected to deluge decontamination while it is manipulated. In some embodiments in which instrument manipulation occurs during operation of deluge decontamination means of the apparatus, the instrument being manipulated is immersed in a reservoir e.g. ultrasonic reservoir below the deluge decontamination means, with or without the application of ultrasonic waves to the fluid in the reservoir. In some embodiments, in which automatic instrument manipulation takes place while the instrument being manipulated is immersed in a reservoir of fluid, deluge decontamination means is additionally operated e.g. in a deluge decontamination region above the reservoir.

While in preferred embodiments the decontaminating apparatus is arranged to provide wet decontamination i.e. decontamination types which involve instruments to be cleaned contacting liquid, the invention is also applicable to other types of decontaminating apparatus which may be arranged for "dry" decontamination only e.g. sterilization apparatus. Preferably however the decontamination apparatus is for the wet decontamination of instruments and comprises means for providing wet decontamination of instruments therein.

The decontaminating apparatus may be configured for providing one or more type of decontamination. Thus, while in preferred embodiments multiple types of decontamination may be provided, in other embodiments, the apparatus may be configured to provide only one or certain types of decontamination. For example, the apparatus may be an ultrasonic decontamination apparatus.

In accordance with the invention in any of its aspects or embodiments, the decontaminating apparatus may comprise a decontaminating chamber in which the instrument is mounted for decontamination. The chamber may provide a fluid tight chamber in which instruments may be decontaminated. Automatic manipulation of the instrument occurs while the instrument is in the chamber. The chamber may define one or more decontaminating regions.

The manipulation of the instrument in accordance with the invention in any of its aspects or embodiments is an automatic manipulation and occurs without manual intervention. The instrument manipulation means of the apparatus is configured to provide such manipulation. In embodiments the automatic manipulation of the instrument or the means for automatically manipulating an instrument, is activated automatically during the automated cycle. This may occur at one or more times during the cycle. The means may be activated intermittently during the cycle e.g. at any of the point(s) outlined above. In embodiments the means is therefore arranged to intermittently be activated for manipulation of the instrument and the method may comprise intermittently manipulating the instrument during the cycle. Intermittent operation may involve two or more operations of the means. However the instrument manipulation means is operated, preferably operation of the means occurs under the control of a set of one or more processors. The set of one or more processors may be configured to provide cycle control of the automated decontaminating cycle. In accordance with any of the embodiments of the invention, manipulation of an instrument may occur while the instrument is fluidly sealed within a decontaminating chamber of the apparatus i.e. while the entire instrument is within the chamber. In embodiments the manipulation occurs within e.g. entirely within a decontaminating chamber of the apparatus.

Preferably the step of manipulating the instrument comprises interacting with the instrument to transmit motion thereto for causing relative movement between two or more relatively movable parts of the instrument, and the instrument manipulation means comprises means for interacting with an instrument to transmit motion to the instrument to cause relative movement between two or more relatively movable parts thereof. The motion transmitted to the instrument is generated externally to the instrument and transmitted thereto by the instrument manipulation means interacting with the instrument. Preferably the method comprises engaging the instrument to transmit the motion thereto, and the means for manipulating the instrument comprises means for engaging an instrument to transmit motion thereto for causing relative movement between two or more relatively movable parts thereof. The engagement may be a direct engagement. The engagement is preferably a mechanical engagement, although it is envisaged that other arrangements e.g. magnetic engagement might be used. The method may comprise matingly engaging the instrument to transmit motion thereto. In embodiments the step of engaging the instrument comprises contacting the instrument to transmit motion thereto. In embodiments the method comprises interacting with the instrument to transmit motion to at least one movable part of the instrument, and preferably engaging the at least one movable part to transmit the motion thereto to cause relative movement between the movable part and another part of the instrument, and the instrument manipulation means is arranged for so doing. The instrument may comprise one or more movable parts and thus any one or more of the movable parts may then be engaged to transmit motion thereto. The instrument might include only a single movable part that is engaged. The method may comprise engaging at least one movable part of the instrument and transmitting motion thereto to cause relative movement between the movable part and another part of the instrument.

Thus, the manipulating means preferably interacts with the instrument to directly cause relative movement between two or more relatively movable parts thereof, and the method comprises such a step. This may be referred to as "direct interaction". Additional relative movement may be provided indirectly between other relatively movable parts of the instrument as a result of the relative movement created between two or more relatively movable parts as a result of the motion transmitted to the instrument by interaction therewith e.g. by instrument engagement means of the instrument manipulation means. Thus the instrument manipulation means transmits motion to the instrument or directly interacts with the instrument to provide relative movement between two or more relatively movable parts thereof, but the two or more parts between which relative movement is provided in accordance with the invention may further comprise additional relatively movable parts between which relative movement is indirectly provided as a result of motion transmitted to the instrument by the interaction between the instrument manipulation means and the instrument. Motion may be transmitted internally between parts of the instrument to create this further relative movement. For example motion may be transmitted to one or more other parts for causing relative motion between further relatively movable parts by an operation transmission mechanism of the instrument.

The parts between which relative motion is provided through direct interaction i.e. by the manipulation means interacting with the instrument to transmit motion thereto may comprise a first set of relatively movable parts as described below in embodiments involving relative movement between the parts of multiple sets of relatively movable parts. The motion transmitted to the instrument may cause movement of one of the first set of relatively movable parts. Where relative movement is provided between other relatively movable parts of the instrument indirectly as a result thereof, the other parts may comprise additional e.g. second or third set of relatively movable parts as described in the embodiments below involving multiple sets of relatively movable parts.

Of course, relative movement may be caused "directly" between more than one set of relative movable parts of the instrument, and the instrument manipulation means may be arranged to interact with the instrument to provide relative movement directly between multiple sets of relatively movable parts e.g. by engaging different portions of the instrument or movable parts thereof. Also it is not necessary that the instrument includes parts between which relative motion is indirectly provided. However, preferably relative movement is "directly" provided i.e. by interaction of the instrument manipulation means with the instrument between two or more parts of the instrument.

References to relative movement being "provided" between parts in accordance with the invention therefore encompass cases in which the movement is directly or indirectly provided unless the context demands otherwise herein.

The relative movement between parts of the instrument that is provided as a result of manipulation of the instrument during the decontamination cycle in accordance with the invention in any of its aspects may involve relative movement between one or more sets of relatively movable parts of the instrument i.e. between the relatively movable parts within a set. It will be appreciated that references to providing relative movement between a plurality of sets of relatively movable parts refer to providing relative movement between the individual parts within each set of parts rather than between the first and second sets of parts if this is not explicitly stated. Of course, relative movement between parts of each set of parts may also result in there being relative movement between parts from the different sets. Each set of relatively movable parts may be or comprise a pair of parts, or may comprise two or more parts.

In embodiments in which the instrument is manipulated to cause relative movement between the parts of a first set of relatively movable parts and between the parts of one or more additional sets of relatively movable parts, the relative movement between the parts of each set of parts may occur substantially simultaneously or sequentially. Where motion is transmitted from one set of parts to another e.g. within the instrument there may be some transmission delay.

In some embodiments the method comprises automatically manipulating the instrument to provide relative movement between relatively movable parts of each of a plurality of sets of relatively movable parts of the instrument, preferably between the relatively movable parts of a first set of relatively movable parts and between the relatively movable parts of at least one additional set of relatively movable parts which may be remote from the first set of relatively movable parts.

In some embodiments relative movement may be provided between the parts of a first set of relatively movable parts and between the parts of a second set of relatively movable parts remote therefrom, and optionally between the parts of a third set of relatively movable parts between the first and second sets of relatively movable parts. The sets of parts may be located at different positions along a length of the instrument. In embodiments the first set of parts may be at a proximal end of the instrument, and the second set of parts at a distal end of the instrument, with the third set of parts where provided, being between the proximal and distal ends of the instrument. The or an additional set of relatively movable parts may include no part in common with the first set of relatively movable parts.

In embodiments in which relative movement is provided between the parts of multiple sets of relatively movable parts, the method may comprise independently causing the parts of each set of parts to move relative to one another, and the manipulation means may be arranged for so doing. For example, the manipulation means may comprise means for directly interacting e.g. engaging different portions of the instrument for providing relative movement between the parts of different sets of relatively movable parts thereof.

However, preferably the method comprises manipulating the instrument to cause relative movement between the parts of a first set of relatively movable parts of the instrument, wherein relative movement between the parts of the first set of parts results in relative movement between the relatively movable parts of the or each additional set of relatively movable parts e.g. between the parts of the second and third sets of relatively movable parts in the embodiments above. The, each or an additional set of relatively movable parts may be remote from the first set of parts. The instrument manipulation means may be configured for carrying out such steps. The step of transmitting motion to the instrument for causing relative movement between the parts of the first set of relatively movable parts may be carried out by transmitting motion thereto in any of the manners described above e.g. by engaging one or more movable part of the first set. Thus the instrument manipulation means interacts directly with the instrument to cause relative movement between parts of the first set of relatively movable parts, and provides the relative movement between the or each additional set indirectly.

Accordingly, preferably the step of manipulating the instrument comprises interacting with the instrument to transmit motion thereto for providing relative movement between the first set of relatively movable parts, and the instrument manipulation means comprises means for interacting with the instrument to transmit motion thereto for providing relative movement between the first set of two or more relatively movable parts. The motion transmitted to the instrument is generated externally to the instrument and transmitted thereto by the instrument manipulation means. Preferably the method comprises engaging the instrument to transmit the motion thereto for providing relative movement between the parts of the first set, and the means for manipulation the instrument comprises means for engaging the instrument to transmit motion thereto for so doing. The engagement is preferably a mechanical engagement, although it is envisaged that other arrangements e.g. magnetic engagement might be used. In embodiments the step of engaging the instrument comprises contacting the one or more of the first set of parts of the instrument to transmit motion thereto. In embodiments the method comprises interacting with the instrument to transmit motion to a (or at least one) movable part of the first set of parts of the instrument, and preferably engaging the (at least one) movable part to transmit the motion thereto to cause relative movement between the movable part and another part of the first set of relatively movable parts of the instrument, and the instrument manipulation means is arranged for so doing.

In embodiments the or each additional set of relatively movable parts e.g. a second or third set of such parts where provided is operably coupled to the first set of relatively movable parts, such that relative movement caused between parts of the first set of relatively movable parts results in relative movement between the, each or an additional set of relatively movable parts. The operable coupling may be arranged to transmit motion between one or more of the first set of parts and one or more of the second set of parts. The operable coupling is a coupling of the instrument. Where a third set of parts is provided between the first and second sets of parts, the third set of parts may be arranged to operably couple the second set of parts to the first set of parts such that relative movement caused to occur between the parts of the first set of parts results in relative movement between parts of the third set of parts and also the second set of parts remote from the first set of parts.

Arrangements in which relative motion caused to occur between parts of a first set of relatively movable parts of the instrument results in relative movement between one or more additional sets of relatively movable parts of the instrument are beneficial, as movement caused at one portion of the instrument may indirectly cause relative movement at other locations, revealing additional surfaces for decontamination in different regions of the instrument at once.

In accordance with the invention in any of its aspects or embodiments, the medical instrument that the apparatus is arranged to manipulate, or that is manipulated in accordance with the method of the present invention, may be any type of medical instrument having relatively movable parts. The instrument is preferably a surgical instrument. The medical instrument in accordance with any of the aspects or embodiments of the invention may be an elongate medical instrument. In embodiments the medical instrument comprises a proximal end and a distal end.

The relative movement provided between two or more parts of the instrument in accordance with the invention in any of its aspects or embodiments preferably comprises relative movement between parts involved in providing a manipulation of a working portion of the instrument in use. The manipulation of the working portion may provide an actuation of the working portion. The working portion of the instrument may or may not be present during automatic manipulation of the instrument. Thus the working portion may or may not be connected to the instrument, but preferably is present. Thus, the instrument preferably comprises a working portion, and the relative movement that is provided is a relative movement between parts involved in providing a manipulation of the working portion in use. Some instruments include a working portion that is detachable for decontamination separately from a remainder of the instrument. However, the automatic instrument manipulation means of the present invention provides the ability to effectively decontaminate a working portion together with the remainder of the instrument avoiding the need to remove the working portion, and the instrument may be decontaminated, and subjected to automatic manipulation with the working portion connected thereto.

Where the instrument comprises a working portion (connected thereto) during automatic manipulation thereof, the working portion may be integral with the instrument or may be a separate piece attached thereto. Thus the connection of the working portion to the remainder of the instrument may be a permanent or detachable connection. Where a working portion is not present, the invention may result in relative movement between parts which would provide a manipulation of a working portion e.g. in any of the manners described, when connected to the instrument in use e.g. to a distal end thereof. Any references to manipulation of the working portion, or relative movement between parts which may provide such manipulation should be understood as equally applying to providing relative movement that will result in such manipulation when a working portion is connected to the instrument in use in embodiments where it is not present.

The relative movement between parts involved in providing a manipulation of a working portion of an instrument in use, and which is preferably provided by the instrument manipulation means, may comprise relative movement between parts of the instrument at least at an operating portion for controlling manipulation of a working portion of the instrument in use, and preferably between relatively movable parts of a working portion or working end of the instrument, or between the working portion and another part of the instrument. In preferred embodiments the operating portion is configured for providing remote control of the manipulation of a working portion of the instrument in use.

In some embodiments the operating portion is configured for providing remote control of the manipulation of a working portion of the instrument in use via an operation transmission arrangement, and the relative movement that is provided by the instrument manipulation means preferably further comprises relative movement between parts of the operating transmission arrangement. The relative movement is a movement that may result in the manipulation of the working portion when present, or, alternatively, would result in the manipulation of the working portion when connected to the instrument.

In accordance with any of the embodiments, the working portion is preferably at a working end of the instrument, e.g. the distal end thereof. The operating portion is preferably at a proximal end of the instrument i.e. an end opposite to the working end. An operating transmission arrangement where provided may extend between the proximal and distal ends of the instrument e.g. between the working portion and the operating portion. The operating portion may be located at an operating end of the instrument.

A manipulation of a working portion of an instrument may involve relative movement between parts of a working portion of the instrument and/or between one or more parts of a working portion and another part of the instrument e.g. a part of the instrument to which the working portion is connected. In the latter case, the other part of the instrument may be a shaft of the instrument e.g. a distal end thereof to which the working portion is connected. In embodiments in which relative movement is provided between a part of the working portion and another part of the instrument, the other part of the instrument may remain stationary. The present invention may involve providing relative movement between any parts involved in providing such a manipulation, including those parts at the working portion where present.

Accordingly, in the invention of any of its embodiments, the relative movement provided by the instrument manipulation means may involve the movement of at least one part of a working portion or between parts of the instrument that would result in such movement when a working portion is connected thereto in use.

In preferred embodiments therefore relative movement is provided at least between parts at a working end of the instrument. The working end may comprise the working portion and/or means for connecting the instrument to a working portion. Alternatively or additionally relative movement may be provided at least between parts of the instrument at a distal end of the instrument. The distal end may be a working end comprising a working portion and/or means for connecting the instrument to a working portion. It will be appreciated that the working portion refers to the portion of the instrument that is e.g. intended to interact with a body or other object in use. The working portion is typically remote from an operating end. For example a working portion may be provided at a distal end of an instrument with a proximal end being an operating end. The operator or operating end may be operated by a human or actuating device as discussed below.

In preferred embodiments relative movement provided between parts of the instrument involving a part or parts of a working portion or at a working end thereof is provided indirectly, and the second set of parts outlined above may comprise such parts.

In some preferred embodiments relative movement between parts provided by the instrument manipulation means or in accordance with the method of the invention provides a change in configuration and/or an articulation of a working portion of the instrument, or would result in such a change or articulation when a working portion is attached to the instrument. The change in configuration may be any change in the relative positions of parts of the working portion. The change in configuration may comprise an extension or retraction of a part e.g. of the working portion and/or an opening or closing between parts. For example, the change in configuration may be an opening or closing of the parts e.g. between the blades of a pair of scissors. The relative positions may be relative rotational or translational positions. The change in configuration may provide an actuation of a working portion of the instrument. A change in configuration may involve relative movement between two parts of the working portion.

In preferred embodiments in which the relative movement between parts of the instrument provides an articulation of the working portion, the articulation may be about a joint or joints. The joint(s) may be of any suitable type. The joint may connect a working portion to a body of the instrument e.g. to a shaft. The joint might be a pivot joint. This would be the case e.g. for a scissor like instrument. In embodiments the joint may comprise any or all of a pivot, hinge or ball and socket joint. In preferred embodiments, however, the joint is a wrist. A working portion of an instrument having a portion that is articulated in accordance with the invention may be arranged to have one or more degrees of freedom, preferably a plurality of degrees of freedom, for example at least 5 or at least 7 degrees of freedom.

Preferably the instrument comprises a working portion.

The working portion may be of any type having utility in the medical e.g. surgical field. In preferred embodiments the working portion is a surgical working portion. By way of example, the working portion may comprise scissors, a grasper, retractor, stabilizer, cautery implement, clamp, stapler, or needle holder. The working portion might be the working portion of a conventional pair of scissors i.e. the blades thereof. In some embodiments the medical instrument is a surgical instrument for use in robot assisted surgery. In these preferred embodiments, the instrument may comprise a working portion in the form of an end effector. Whatever the nature of the instrument, the working portion may be provided as a separate piece removably attached to the remainder of the medical instrument e.g. to a distal end of a shaft. This may allow interchanging of different types of working portion as desired. The instrument may comprise means for connecting the instrument to a working portion. The means may be any suitable connection and may be located at the distal or working end thereof.

Preferably the relative movement provided between parts of an instrument in accordance with the invention alternatively or additionally comprises relative movement between parts of an operating portion of the instrument. The operating portion forms part of an operating mechanism of the instrument. The operating portion may be manually operable, or may be configured to be operable via an actuating device. The operating portion provides the ability to control a working portion of the instrument in use (when connected to the instrument). Preferably such movement is caused directly by interaction of the instrument manipulation means with the operating portion. In embodiments the instrument manipulation means is arranged to interact with the operating portion of an instrument to transmit motion to a part of the operating portion, and preferably engages a part or parts of the operating portion to provide relative motion between parts thereof.

Where relative movement is provided between multiple sets of parts in accordance with the invention, preferably the first set of parts comprises parts of the operating portion. Accordingly, in some embodiments the instrument comprises an operating portion for remotely controlling manipulation of a working portion of the instrument, wherein the first set of parts comprises a part or parts of the operating portion, and the second set of parts comprises a part or parts of the working portion of the instrument.

In preferred embodiments the operating portion is arranged for remotely controlling manipulation of a working portion of the instrument in use (at least when connected to the instrument in embodiments where the instrument has a detachable working portion) e.g. remotely controlling relative movement between parts including one or more parts of a working portion of the instrument. The relative movement involving the part or parts of the working portion may be of any of the types discussed above and may provide e.g. an articulation of or change in configuration at the working portion of the instrument. References to the operating portion being arranged for remotely controlling manipulation of a working portion do not require that the working portion is necessarily present. The instrument may or may not comprise the working portion during manipulation.

In preferred embodiments the operating portion comprises parts that are movable relative to one another to remotely control manipulation of a working portion of the instrument (at least when the working portion of the instrument is connected thereto in embodiments where the instrument has a detachable working portion) e.g. to control relative motion between parts of the instrument including one or more parts of the working portion. The present invention preferably comprises providing relative movement between such relatively movable parts of the operating portion, preferably by engaging the operating portion, e.g. one or more of the relatively movable parts thereof. The relatively movable parts of the operating portion are remote from the working portion of the instrument.

One or more of the relatively movable parts of the operating portion thereof may be movable. For example one or more movable dials may be provided which are movable relative to a base for controlling operation of a working portion, or relatively movable handles may be provided such as in the case of a pair of scissors. Other examples of movable parts might include handles, wheels, a slider, etc or combinations thereof. In embodiments the operating portion comprises one or more parts that are movable to control operation of the working portion. In preferred embodiments the method comprises interacting with e.g. engaging one or more movable part of the operating portion to transmit motion thereto.

The relatively movable parts of the operating portion may be relatively rotationally and/or translationally movable. The relatively movable parts of the operating portion may be manually operable or may be intended to be operable by a device connected thereto in use to provide relative movement therebetween. The operating portion may be manually operable or may be configured to be operable via an actuating device e.g. robot manipulator as described below.

In preferred embodiments the operating portion comprises an operating interface and/or handle portion comprising the relatively movable part or parts. A handle portion may comprise one or more handles. The relatively movable parts of a handle portion may be a pair of handles of the handle portion e.g. in the case of a pair of forceps or scissors. In other arrangements the handle portion may comprise more complex manually actuable controls e.g. wheels, dials, buttons etc to provide control over complex aspects of the manipulation and actuation of a working portion e.g. as known in the art of laparoscopic instruments. A handle portion may comprise an operating interface.

Preferably the relative movement provided between parts of an instrument in accordance with the invention comprises relative movement between parts of a handle portion and/or operating interface of the operating portion e.g. mechanism. In use a desired operation may be indicated i.e. input via the interface or handle portion by controlling the relative positions of the parts thereof. The interface or handle portion is arranged to receive an input indicative of an operation to be performed at the working end or portion of the apparatus. In embodiments, therefore, the method comprises providing relative movement between parts of an operating interface or handle portion of the operating portion. The handle portion or interface is remote from a working portion of the instrument for providing remote control of the manipulation thereof. In accordance with the invention in any of its embodiments, where provided, an operating interface or handle portion is preferably located at a proximal end of the instrument and the working portion at a distal end thereof.

Where provided, an interface of the operating portion may be manually operable in use of the instrument. The interface may be a user interface. A handle portion would similarly be manually i.e. user operable. The interface or handle portion may comprise one or more wheels, dials, buttons, graspable levers etc. For example, this may be the case for some instruments intended for use in laparoscopic or other minimally invasive techniques, or for simple forceps, scissors or similar.

In other arrangements the operating portion or an interface of the operating portion may be intended to be manipulated via a device connected thereto e.g. a robotic manipulator for remotely controlling manipulation of a working portion of the instrument. The relatively movable parts of the interface may be arranged to be engaged by one or more servomotor actuators. Examples of such instruments are those used in so-called "robot assisted surgery". A surgeon may then control relative movement between parts at a working portion of the instrument by controlling the device e.g. robotic manipulator directly e.g. using a joystick or similar, of via a computer. The latter option may enable telesurgery to be carried out, with the surgeon not necessarily in the same room as the patient. In some embodiments the instrument may comprise a connection hub having the operating interface. A movable part may be of any configuration to provide a surface that is movable relative to another part of the interface. The interface may be configured for mating to an actuation device such as a robotic manipulator. In these arrangements the interface may comprise one or more moving parts. It may comprise one or more dials, balls, wheels etc, or may comprise one or more movable plate. In general the interface where actuated by a device may be any suitable input interface for receiving an indication indicative of an operation to be performed as known in the art.

In some embodiments, whether the instrument is manually controlled or controlled via a device, the instrument manipulation means is arranged to mate with the operating portion or an interface or handle portion of the operating portion for transmitting motion to one or more parts of thereof for providing relative movement between parts thereof.

The instrument may further comprise operation transmission means for causing an operation e.g. manipulation such as an actuation or articulation indicated at an operating portion e.g. a handle portion or interface thereof to be effected at a working portion remote from the operating portion e.g. interface or handle portion (when a working portion is connected to the instrument). The transmission means is preferably a transmission mechanism, and may be of any suitable form. Thus the operating portion preferably comprises an interface or handle portion having parts that are movable relative to one another to provide an indication of an operation to be performed by a remote working portion, and operation transmitting means for causing the operation to be performed at the remote working portion. In embodiments the transmitting means uses motion imparted at the operating portion e.g. interface or handle portion thereof to effect the operation at the remote working portion. The transmission means may be arranged to use relative movement involving a part or parts of the operating portion e.g. interface or handle portion thereof to provide relative motion involving a part or parts of the working portion of the instrument. The transmitting means may comprise an articulation or actuation transmission mechanism. The transmitting means may extend along an internal passageway or passageways of the instrument. In some preferred embodiments the transmitting means comprises one or more, and preferably a plurality of cables or rods e.g. extending between the operating portion e.g. interface or handle portion thereof and the working portion or a connection therefor. The medical instrument may comprise a connecting portion connecting an operating portion e.g. interface or handle portion of the operating portion to the remote working portion, the connecting portion comprising the operation transmitting means. The connecting portion may comprise a shaft. For example, the connecting portion may comprise one or more internal passageways that accommodate components of the operation transmission means e.g. cables extending between the operating portion or interface or handle portion thereof and the remote parts. The connecting portion may be of any suitable length.

In some embodiments therefore, the operating portion is arranged to provide remote control of operation of a working portion via operation transmission means, and comprises an operation interface or handle portion for providing an indication of an operation to be effected at the working portion. The instrument may or may not comprise the working portion during manipulation, and thus the operating portion may be arranged to provide remote control of operation of a working portion via operating transmission means when the working portion is connected thereto. The relative motion provided between two or more parts of the instrument in accordance with the invention preferably includes relative motion between parts of the operating portion e.g. handle portion or interface and between parts of the operation transmission means. In some embodiments relative movement in accordance with the invention is provided between the parts of a first set of relatively movable parts and between the parts of a second set of relatively movable parts remote therefrom, and between the parts of a third set of relatively movable parts between the first and second sets of relatively movable parts. In these embodiments the first set of parts may comprise a part or parts of the operating portion e.g. the interface or handle portion thereof, the second set of parts comprises a part or parts of the working portion of the instrument when present, and the third set of parts comprises a part or parts of the operation transmission means.

Relative movement between parts of the instrument provided during decontamination in accordance with the invention may, in these preferred embodiments, ensure that different surfaces not only of the working portion when present, but also of the operation transmission means and operating portion e.g. interface or handle portion thereof are exposed for cleaning.

Regardless of how it is operated, the operating portion may be an actuation e.g. articulation transmission means e.g. mechanism for remotely controlling actuation or articulation of a working portion of the instrument, and the interface where provided may be an actuation or articulation transmission interface. The operating portion and, where provided, operation transmission means, preferably comprise or consist of mechanical operating mechanisms or operation transmission mechanisms. In other words, actuation of the operating portion enables remote manipulation of the working portion of the instrument via a mechanical arrangement, and the operating portion may comprise a mechanically operated handle portion or interface.

In some arrangements the operating portion, or an interface or handle portion thereof, is at a proximal end of the instrument and the working portion is at a distal portion of the instrument. Of course, one or both of an operating portion e.g. handle portion or interface thereof and working portion of an instrument need not be located at an end of an instrument. Thus a working portion may be located at a distal end of the instrument and/or an operating portion e.g. handle portion or interface thereof may be located at a proximal end of the instrument.

In general, the relative movement provided between parts of the instrument in accordance with the invention may comprise relative movement between any or all of; parts of a working portion of the instrument (where present), one or more parts of a working portion and another part of the instrument, parts of an operating portion, e.g. between parts of an operating interface or handle portion and/or parts of an operation transmission means, of the instrument. In some embodiments only the relative motion between parts of the operating portion is provided directly through interaction or engagement between the automatic manipulation means and the instrument. In embodiments in which a working portion is not present, the embodiments described above involving relative movement between parts of an operating portion or operation transmission would be unaffected, and would involve movement that would result in the movement described of a working portion when connected to the instrument in use. In preferred embodiments, however, the instrument that undergoes manipulation includes the working portion, and the methods described herein involve an instrument having a working portion. References to the relative movement being movement that is involved in manipulation of a working portion, or of an operating portion being arranged to provide manipulation of a working portion in use, do not require that the working portion is present if this is not explicitly stated, and cover the case in which the movement would result in manipulation of the working portion etc, although in embodiments, the instrument does comprise the working portion e.g. connected thereto whether integrally formed therewith or being a separate component attached thereto.

In general it may be seen that in accordance with any of the aspects or embodiments of the invention the automatic manipulation means of the present invention preferably interacts e.g. engages with a part or parts of an operating mechanism of the instrument to provide relative movement at least between parts of the operating mechanism.

Various types of medical instrument comprise parts between which relative motion may occur in use, and which may be operated via a operating portion remote from a working portion thereof. The method and apparatus of the invention may be used in conjunction with any such instrument. In accordance with the invention, the medical instrument may be a laparoscopic instrument, an instrument for use in minimally invasive surgery, an endoscopic instrument or an instrument for use in robot assisted surgery. The medical instrument may be an instrument used in telesurgery. While the present invention has particular application to more complex surgical instruments, or remotely operated instruments, it will be appreciated that in other arrangements, the medical instrument might be forceps, scissors or other such instruments having relatively movable parts. For example, scissors have a working portion i.e. blades that are remotely operated via an operating portion in the form of handles. However, other instruments may be manipulated in accordance with the invention that are not remotely operated.

The relative motion provided between parts of the instrument in accordance with the invention may comprise rotational or translational relative movement, or combinations thereof, and the instrument manipulation means may be arranged to provide such movement. In preferred embodiments the method comprises providing relative rotational motion between two or more parts of the instrument, and the manipulation means is arranged to interact with the instrument to transmit motion thereto for providing such relative rotational movement. However, it will be appreciated that the type of movement imparted will depend upon the type of instrument to be manipulated e.g. the configuration of an operating portion thereof. For example, this may depend upon whether movable parts of an operating interface or handle are configured for rotation or sliding.

In preferred embodiments method comprises manipulating the medical instrument to provide relative movement between the two or more parts corresponding to a full range of relative movement that would occur in use of the instrument. In preferred embodiments in which relative movement is provided between parts of an operating portion e.g. handle interface of the instrument, preferably one or more, and most preferably each movable part thereof is moved between positions corresponding to a full range of motion thereof. In this way, more thorough cleaning of the instrument may be achieved. The method may comprise providing relative movement between parts of an operating portion which will result in different modes of operation of a working portion of the instrument e.g. actuation, articulation, change of angle, opening/closing etc.

The method may comprise providing a reciprocating relative movement between the two or more parts.

In accordance with the invention, as discussed above, the instrument manipulation means preferably comprises means for transmitting motion to the instrument for causing relative movement between two or more parts of the instrument in use. Preferably the means engages the instrument, or at least a portion thereof, to transmit motion thereto. Preferably the means engages only a portion or portions of the instrument for transmitting motion thereto. This may provide relative movement between two or more parts via the "direct" interaction mode. The instrument engaging means preferably engages at least one movable part of the instrument to transmit movement thereto for causing relative movement between the part and another part of the instrument.

The instrument manipulation means may be arranged to transmit rotational and/or translational movement to the instrument depending upon the relative movement that is to be produced in the instrument. In preferred embodiments the instrument manipulation means is arranged to transmit rotational movement to the instrument for causing relative movement between two or more parts thereof.

In embodiments, the engaging means of the instrument manipulation means preferably comprises one or more instrument engaging surfaces that are movable to transmit motion to an instrument engaged therewith in use. The or each surface may therefore be rotationally and/or translationally movable, and is preferably rotationally movable. The or each surface is movable in a manner to transmit a desired type of motion to an instrument. The instrument engaging surface or surfaces may include planar or curved surfaces. The or each surface engages a part or parts of the instrument to transmit movement thereto for causing relative movement between parts of the instrument.

The instrument engaging surface(s) are preferably provided by one or more instrument engaging elements. The instrument engaging means of the instrument manipulation means thus preferably comprises one or more movable instrument engaging elements, each defining one or more instrument engaging surfaces, the or each instrument engaging element being movable to transmit motion to an instrument engaged therewith in use. Movement of the element may provide corresponding movement of its surface. Thus an instrument is engaged with a surface or surfaces of the or each engaging element in use. The or each engaging element may be movable to transmit a corresponding movement to a portion of an instrument engaged therewith in use. The or each engaging element may be arranged to be rotationally and/or translationally movable to transmit a rotational and/or translational movement to the instrument depending upon the type of movement intended to be transmitted to the instrument. In preferred embodiments the or each engaging element is arranged to be rotationally movable. In preferred embodiments the each or an instrument engaging element is arranged to be movable in a circular path for imparting circular motion to a part of the instrument.

In preferred embodiments, the or each instrument engaging element is arranged to engage a movable part of the instrument for transmitting motion thereto for providing relative movement between the part and another part of the instrument. In some embodiments the or each instrument engaging element is arranged to receive or be received by a movable part of the instrument. The or each instrument engaging element may, for example comprise a pin, ball, socket, plate etc.

In some embodiments a plurality of instrument engaging elements are provided that are movable to transmit motion to an instrument. The instrument engaging elements may be of the same or differing construction, and may be arranged to move in the same or differing manners. Any of the features described herein in relation to an instrument engaging element may apply to the, each or an engaging element where present.

Where a plurality of movable instrument engaging elements are provided, the instrument engaging elements may or may not be independently movable. Thus, the elements may be configured to be movable together or separately. The instrument engaging elements may or may not be movable (rotationally or translationally) relative to one another. In some embodiments, the plurality of instrument engaging elements may be coupled to one another such that the elements move together. The elements may then be collectively driven.

In some embodiments it is envisaged that one or more fixed instrument engaging element may be provided in addition to one or more movable instrument engaging element. The engaging elements may then engage respective parts of the instrument to create relative motion therebetween when the movable element is moved. Such an arrangement might enable movement between scissor handles to be provided. Alternatively a part of an instrument may be fixed to a fixed part of the decontaminating apparatus to allow relative movement to be created using a movable element, without the manipulation means needing to include a fixed instrument engaging element.

The or each movable instrument engaging element may or may not be arranged to move through a limited range of motion. For example, the or each instrument engaging element may be arranged to be rotatable through a limited angular range for transmitting rotational motion to an instrument. For example, rotation may be semi-rotation or through another range less than 360 degrees. In other arrangements the or each instrument engaging element, may be freely rotatable. In some arrangements the or each instrument engaging element, may be arranged to be reciprocably movable.

The degree of motion of an engaging element, and the type of motion, may be chosen as desired depending upon the required degree and type of motion that needs to be imparted to the part(s) of the instrument with which the element is to be engaged for causing relative motion between parts thereof. In some arrangements, the degree of motion of the or each engaging element may be chosen to provide relative movement between the parts of an instrument corresponding to a full range of motion that may be encountered in the use of the instrument.

In some preferred embodiments the instrument manipulation means is arranged to matingly engage the instrument e.g. a part or parts thereof for transmitting motion thereto. In some embodiments the or each instrument engaging means is thus configured for mating with a portion of an instrument for transmitting motion thereto. The instrument engaging means may therefore comprise one half of a plug and socket or ball and socket type connection. Where the engaging means comprises one or more instrument engaging elements, the or each element may be configured to mate with a portion of the instrument. For example, the or each element may be or comprise male or female mating means.

In accordance with the invention the instrument engaging means e.g. element(s) may engage any portion of an instrument for causing desired relative movement between parts thereof. Preferably the instrument engaging means is arranged to engage with an operating portion e.g. with an operating interface or handle portion of the operating portion of the instrument for transmitting motion thereto for creating relative movement between parts of the operating portion or interface or handle portion thereof as discussed above. Preferably the instrument engaging means or element(s) are arranged to engage one or more movable parts of the operating portion, preferably an interface or handle portion thereof, for transmitting motion thereto to cause relative movement between the part or parts and another part of the operating portion e.g. interface or handle portion thereof. While engagement might also be made with other parts of an instrument e.g. with a working portion, or operation transmission arrangement, in preferred embodiments relative movement between parts at these portions of the instrument is achieved indirectly.

The instrument manipulation means is arranged to be driven for providing movement thereto that may used in providing the motion that is transmitted to an instrument via the instrument engaging means in use. The instrument manipulation means may be connected to driving means for driving the manipulation means. The apparatus may further comprise such driving means.

The instrument manipulation means may be driven in any suitable manner, and the method may comprise driving the automatic manipulation in any such manner. For example, the means may be electrically driven. However, preferably the means is magnetically or hydraulically driven, and the automatic manipulation of the instrument performed in accordance with the method is magnetically or hydraulically driven. Magnetic or hydraulic arrangements are preferred as they are more compatible with wet decontamination processes. It will be appreciated that in the context of wet decontamination, it is desirable to avoid the presence of electrical components within the decontamination chamber. If electrically driven arrangements are used, it may be necessary to provide an operable connection between the manipulating means and an electrical motor located externally to the decontamination chamber e.g. through a wall thereof. This would require modification of the chamber wall, and present additional challenges in sealing the connection. In the case of magnetically driven arrangements, the instrument manipulation means may be driven by a magnetic driving arrangement located externally to the decontamination chamber that is magnetically coupled to the instrument manipulation means through a wall of the chamber. These arrangements are preferable to electrically driven arrangements, as they avoid the need to modify the wall of the chamber or create an opening therethrough. For example, a magnetic coupling may be achieved through a stainless steel chamber wall.

Hydraulically driven arrangements are particularly preferred as they may be implemented internally to the chamber, making it possible to implement the invention by means of a simple adaptation of the internal parts of the decontaminating apparatus, and may utilise existing fluid flow paths. In preferred embodiments the instrument manipulation means is arranged to be hydraulically driven by the flow of fluid along a fluid flow path of the apparatus, and the method comprises using a flow of fluid along a fluid flow path of the apparatus to hydraulically drive the automatic manipulation. The flow path is preferably a flow path along which decontaminating fluid flows to provide fluid for decontamination of instruments during the decontamination cycle of the apparatus. The flow path may be a flow path of a fluid supply system of the apparatus along which decontaminating fluid flows for supply to a decontaminating fluid delivery system of the apparatus. Preferably the flow path is a flow path used to supply fluid for use in deluge decontamination. However, the flow path could be used to supply fluid to any other type of decontamination means of the apparatus. In this way, the instrument manipulation means may be driven by tapping into an existing fluid flow path of the apparatus, without the need to provide a dedicated powering arrangement. Thus, in embodiments, the apparatus comprises a flow path along which decontaminating fluid flows to provide fluid for decontamination of instruments during the decontamination cycle of the apparatus, and the manipulation means is preferably driven using a flow of fluid along the path.

In hydraulically driven arrangements, the instrument manipulation means, and preferably a proximal or driven end thereof, may be connected to means for converting energy from a fluid flow into movement that may be used in providing the motion transmitted to instruments by the instrument engaging means. Preferably the movement is a rotational movement. For example, the manipulation means, or a proximal end thereof, may be connected to a water wheel or similar. Such means for converting energy from the fluid flow to movement of the manipulation means may be permanently or removably connected to e.g. a proximal end of the manipulation means. For example, the proximal end may be removably connected to the converting means. This may allow the manipulation means to be removed from the apparatus if desired. In other arrangements the energy converting means may form part of the manipulation means i.e. it may not be removable therefrom. The converting means in combination with fluid flow in use together then provide driving means for the manipulation means.

In other embodiments the instrument manipulation means is driven using ultrasonic energy. In these embodiments the apparatus comprises means for driving the instrument manipulation means using ultrasonic energy. An ultrasonically driven arrangement preferably uses ultrasonic energy provided by ultrasonic waves produced for the ultrasonic decontamination of instruments to drive the instrument manipulation means. The apparatus may comprise ultrasonic decontaminating means in accordance with any of the embodiments described herein.

In general, in ultrasonically driven arrangements, whether or not the ultrasonic driving uses ultrasonic energy of waves produced for use in the ultrasonic decontamination of instruments, the means for driving the instrument manipulation means may comprise means for harnessing the energy of ultrasonic waves produced for use in the ultrasonic decontamination of instruments in the apparatus, for use in driving the instrument manipulation means. The waves may be produced in an ultrasonic reservoir of the apparatus, e.g. in an ultrasonic decontamination region thereof. The driving means may, in embodiments, comprise means, e.g. one or more transducer, for converting the ultrasonic energy of the waves into another form of energy e.g. electrical energy for driving the instrument manipulation means. For example, the converting means may comprise one or more piezoelectric transducer. Electrical energy produced may be used to drive the instrument manipulation means in any suitable manner e.g. via one or more servomotors. Thus, in these embodiments the driving means uses the ultrasonic energy of ultrasonic waves produced for the ultrasonic decontamination of instruments in driving the instrument manipulation means. The ultrasonic waves are produced in the decontamination chamber e.g. in an ultrasonic reservoir of the apparatus. Preferably the means for driving the instrument manipulation means is located fully within the decontamination chamber of the apparatus in these embodiments using ultrasonic energy. For example, the driving means (e.g. one of more transducer and servomotors, where present) may be located in a sealed unit within the chamber. This avoids the need to locate components external to the chamber and make an opening in the wall. Preferably the apparatus additionally comprises one or more ultrasonic wave source, e.g. one or more transducer, which may be located externally to or within an ultrasonic reservoir of the decontaminating apparatus, which causes ultrasonic waves to propagate within the reservoir. This source generates the ultrasonic waves whose energy may then be harnessed to drive the instrument manipulation means. Thus the apparatus preferably further comprises one or more transducer, such as a piezoelectric transducer, for converting electrical energy to ultrasonic energy for producing ultrasonic waves for use in the ultrasonic decontamination of instruments e.g. in an ultrasonic reservoir of the apparatus.

In embodiments, the instrument manipulation means may be hydraulically, magnetically and/or ultrasonically driven, and the apparatus may comprise means for driving the instrument manipulation means in any of these manners. In other embodiments the instrument manipulation means may be alternatively or additionally electrically driven, and the driving means may be configured to additionally or alternatively drive the instrument manipulation means electrically. The instrument manipulation means may be driven using any one or ones of the above mentioned techniques, or using any combination thereof.

In any of the embodiments of the invention, the instrument manipulation means may comprise a shaft that is driven in use. Movement of the shaft may be used in providing motion that is transmitted to the instrument by the engaging means for causing relative movement between parts of the instrument.

The instrument engaging means may be provided at a free end or ends of the instrument manipulation means.

In some embodiments the instrument manipulation means may comprise a driven end and an end comprising the instrument engaging means. The means may define proximal and distal ends. The driven end and instrument engaging ends may then be respectively proximal and distal ends of the means. Where provided, a shaft may be located between and may connect proximal and distal ends of the manipulation means. The distal end may then be a free end.

However, it is driven, the instrument manipulation means. e.g. a proximal end thereof, is driven to impart movement thereto for use in providing the motion that is transmitted to an instrument by the engaging means. The instrument manipulation means is preferably driven to impart rotational movement for use in providing the motion transmitted to an instrument.

It will be appreciated that any suitable intermediate arrangement or arrangements comprising e.g. linkages or gears may be provided between a driven part of the manipulating means and the instrument engaging means to convert movement imparted by driving of the means e.g. a shaft thereof to motion suitable for transmission to the instrument. The instrument manipulation means, or an intermediate arrangement thereof, may comprise one or more pistons and/or a piston and spring arrangement, The intermediate arrangement might, for example, convert a linear motion imparted to the instrument manipulation means by driving means to a rotational movement for transmission to the engaging means, (and hence to the instrument) or vice versa. In some preferred arrangements the intermediate arrangement may convert movement imparted by the driving means to the instrument manipulation means to movement in a different plane and/or direction for transmission to the instrument engaging means. For example, movement of a driven shaft about a horizontal axis may be converted to movement of an engaging element about a vertical axis or vice versa. In embodiments in which the engaging means comprises one or more engaging elements, the or each engaging element may be connected to a distal end of a shaft of the manipulation means. The or each engaging element may be directly connected to the shaft or may be connected via an intermediate arrangement for converting movement of the shaft to desired movement of the engaging element. An arrangement might convert rotational movement e.g. of a shaft about an axis to circular movement of an engaging element. Similarly an intermediate arrangement or arrangements may be used to convert movement occurring as a result of interaction e.g. with a fluid flow to movement suitable for driving a shaft. Thus an intermediate arrangement may be located between the driving means e.g. between means for interacting with fluid flow, and a shaft of the manipulation means that provides movement for use in providing the motion transmitted to the instrument.

In some arrangements the or each instrument engagement element is connected to a rotary cam which is imparted with motion by a shaft of the manipulation means. The or each element may be connected to the cam in a manner such that it is imparted with circular motion. The element may be a pin or ball etc. The or each element may be connected to the shaft by one or more intermediate shafts and/or linkages.

The decontamination apparatus is preferably configured for carrying out at least wet decontamination of instruments, and the automated decontamination cycle preferably involves one or more wet decontamination stages. Accordingly the instrument that is mounted in the apparatus to be decontaminated is preferably suitable for wet decontamination. The medical instrument may be a component of a medical e.g. surgical system that is detached from a remainder of the system for decontamination. The medical instrument may therefore be arranged to be coupled to another device. This may be achieved e.g. via an interface of an operation portion as discussed above. The instrument may comprise a hub at a proximal end thereof for this purpose. Such a coupling may be provided at a proximal end of the instrument having an working portion at a distal end thereof. In embodiments the instrument does not comprise electronic components e.g. circuitry.

The instrument manipulation means is located at least partially within the decontamination chamber for engaging instruments during a decontamination cycle. At least the instrument engaging means thereof is located within the decontamination chamber. It is envisaged that a proximal end thereof may be located outside the chamber e.g. for operable connection with driving means.

However, in preferred embodiments the instrument manipulation means is located entirely within the decontamination chamber. Preferably driving means for the manipulating means is also located within the decontamination chamber. In preferred embodiments the manipulating means is driven hydraulically by a fluid flow path within the decontamination chamber.

The instrument manipulation means is preferably arranged to be removable from the decontamination chamber (and decontaminating apparatus). A driving means may not be removable from the chamber (and apparatus), and, where provided, a means for interacting with fluid flow may not be removable from the apparatus or chamber. The manipulating means may be removable alone, or in combination with a removable part of the apparatus e.g. carrier, basket etc.

In embodiments the decontaminating means of the apparatus comprises decontaminating fluid delivery means for delivering decontaminating fluid to the interior of the decontamination chamber for contacting instruments therein during an automated decontamination cycle. The fluid delivery means may comprise spraying means for providing jets of pressurised fluid e.g. spray arms and/or means for delivering fluid to a reservoir in which instruments may be immersed e.g. for soaking and/or ultrasonic cleaning. The spray arms where provided may be rotatable about an axis e.g. a vertical axis. The fluid delivery means refers to those components of the apparatus that output fluid for contacting instruments in use. The fluid delivery means may form part of a deluge or ultrasonic decontamination means. The decontaminating means may further comprise fluid supply means for supplying fluid to the fluid delivery means.

In some embodiments a fluid supply system of the apparatus may comprise one or more fluid paths for supplying fluid to deluge decontamination means and/or a reservoir e.g. of an ultrasonic decontaminating means of the apparatus and/or one or more fluid paths for supplying fluid to ports to which instruments may be connected for providing fluid to internal surfaces thereof. In embodiments in which the instrument manipulation means is hydraulically driven, the means may be driven by fluid from either of these types of flow path, although preferably a flow path used to supply deluge decontamination means is used.

It will be appreciated that in embodiments, the instrument manipulation means does not form part of the fluid delivery means of the apparatus. The instrument manipulation means does not comprise a flow path along which fluid may flow for output to the interior of the decontamination chamber for contacting instruments therein. The instrument manipulation means may be free from any internal fluid passageway e.g. connecting the proximal and distal ends thereof where provided. In embodiments in which the manipulation means comprises a shaft, the ends of the shaft are not in fluid communication with one another. The shaft may be a solid shaft.

The decontaminating apparatus may comprise one or more type of decontaminating means, and the automated decontamination cycle during which manipulation is performed may comprise one or more decontamination stages as described above. The decontamination apparatus preferably includes one or both of deluge and ultrasonic decontamination means, and the decontamination cycle is preferably a cycle in which instruments under go one or both of deluge and ultrasonic decontamination.

In embodiments the decontamination apparatus e.g. a decontamination chamber thereof may comprise one or both of an ultrasonic and deluge decontamination region. The apparatus will then comprise one or both of ultrasonic and deluge decontamination means as appropriate. It will be appreciated that where both deluge and ultrasonic decontamination regions are provided, separate decontamination chambers may be provided, defining respectively ultrasonic and deluge contamination regions. However preferably the ultrasonic and deluge decontamination regions are provided in the same decontamination chamber.

In embodiments in which both deluge and ultrasonic decontamination regions and means are provided, the instrument manipulation means may be arranged to manipulate instruments when located in either the ultrasonic or deluge decontamination region, or both. The instrument manipulation means may be located in the ultrasonic or deluge decontamination region, or, where instruments are conveyed between the ultrasonic and deluge decontamination regions, may be arranged to be conveyed with the instruments between the different regions to enable manipulation of instruments to be carried out in both regions. Of course, alternatively manipulation means may be provided associated respectively with an ultrasonic and deluge decontamination region.

In accordance with embodiments having an ultrasonic decontamination means and region, whether or not in combination with a deluge decontamination means and region, the ultrasonic decontamination means may comprise a reservoir, and means for applying ultrasonic waves to a decontaminating fluid in the reservoir. Ultrasonic waves may be applied to fluid in the reservoir by means of one or more transducers which may be located adjacent an edge or base of the reservoir, and preferably on the outside of the reservoir. The transducers are preferably provided with an ultrasonic frequency signal from a frequency generator. In some situations, instruments may be immersed in a reservoir of the ultrasonic decontamination means without applying ultrasonic waves to fluid in the reservoir to provide a soaking decontamination stage.

The frequency of the ultrasonic waves is preferably greater than about 15 kHz more preferably greater than about 20 kHz, and ideally between about 25 and 40 kHz.

In preferred embodiments the manipulation means is arranged to provide manipulation of instruments while immersed in the ultrasonic reservoir, with or without the simultaneous application of ultrasonic waves to fluid in the reservoir. Thus the manipulation means may be applied during a soaking stage.

Deluge decontamination means, whether or not provided in combination with ultrasonic decontamination means, may be of any conventional form. As used herein, deluge decontamination involves forcing pressurized fluid over the instruments. The deluge decontamination means where provided comprises spraying means for providing jets of pressurized fluid. The pressure of the jets required to achieve decontamination may be selected as appropriate and, will depend upon factors such as the length of decontamination cycle, size of the apparatus, nature of decontamination fluid etc.

In some arrangements in which both deluge and ultrasonic decontamination means are provided, the decontamination apparatus may comprise an ultrasonic decontamination region located below a deluge decontamination region. In a preferred arrangement, an ultrasonic decontaminating reservoir is located below the deluge decontaminating region in the lower part of the apparatus. For example, the reservoir may occupy the sump area of a cabinet type washer.

In some embodiments the instrument manipulation means is hydraulically powered using a flow path along which fluid is supplied to a deluge decontaminating means. The manipulation means may be activated by activating the deluge decontamination means. In these embodiments the instrument manipulation means may be activated for manipulating an instrument located in an ultrasonic reservoir e.g. for soaking or ultrasonic decontamination when deluge decontamination is activated for deluge decontamination instruments located in a deluge decontamination region above the reservoir. However, any arrangement may be used, and the manipulation means may be independently operable to the deluge decontamination means or any other decontamination means.

The decontaminating apparatus of the present invention may be a cabinet style washer apparatus or may be a chest style apparatus. For example, the apparatus may be a cabinet style washer apparatus having both deluge and ultrasonic decontamination means, e.g. with a deluge decontamination region above an ultrasonic reservoir, or a chest or bath style apparatus having only ultrasonic decontamination means. Of course, while the invention has been illustrated by reference to a decontaminating apparatus and cycle involving deluge and/or ultrasonic decontamination of instruments, it may be implemented in relation to a decontaminating apparatus or cycle that does not include such types of decontamination, or which includes additional types of decontamination. For example, the decontaminating apparatus may alternatively or additionally be configured to provide sterilisation of instruments, and the decontamination cycle be a sterilisation cycle or include a sterilisation stage.

The decontaminating fluid used in accordance with the invention in any of its aspects or embodiments may simply be water, but preferably contains cleaning and/or disinfecting agents.

It will be appreciated that the manipulating means may or may not be activated to transmit motion to instruments simultaneously with activation of the or a decontaminating means of the apparatus during the decontaminating cycle. For example, it may be desirable that the instrument manipulation means is not activated at least at the same time as ultrasonic decontamination means, as this may cause movement of the decontaminating fluid which may interfere with the development of ultrasonic waves. However, in preferred embodiments the manipulation means is activated at the same time as deluge decontamination means. The manipulation means may be driven by a flow path that also supplies the deluge decontamination means. Where deluge decontamination means is operated while instruments are immersed in an ultrasonic reservoir, e.g. above the reservoir, the impact of ultrasonic waves where provided may already be reduced. Thus, in some embodiments the manipulation occurs in relation to instruments immersed in an ultrasonic reservoir while ultrasonic waves are applied, and with the simultaneously operation of deluge decontamination means of the apparatus e.g. to clean instruments above the reservoir.

In some embodiments comprising deluge decontamination means and a reservoir in which instruments may be immersed, with or without the application of ultrasonic waves, fluid from the reservoir may be used to supply the deluge decontamination means.

Preferably the apparatus comprises means for supplying fluid to an internal surface of an instrument. In embodiments the instrument comprises one or more internal passageway, and the method comprises supplying fluid to the interior of the instrument during the decontamination cycle for providing decontamination of internal surfaces of the instrument. The apparatus may be arranged such that fluid may be supplied to the interior of an instrument to be cleaned at any point in a decontamination cycle, and the method may comprise such a step. Fluid may be supplied during ultrasonic or deluge cleaning, or both where the apparatus provides both types of cleaning, or during soaking without ultrasonics. Preferably fluid is supplied to the interior of instruments at least in an ultrasonic decontamination region when present. By filling the inside of the instrument with fluid in this way, ultrasonic decontamination of the internal surface may be obtained, as ultrasonic waves will propagate through the fluid. It is also advantageous to instead, or preferably additionally supply fluid to the internal surface at other times, e.g. in the deluge spraying region where provided, alternatively or additionally to an ultrasonic decontamination region, to provide more thorough decontaminating and removal of debris from the instrument.

In some embodiments fluid may be supplied to the interior of an instrument to be cleaned during activation of the instrument manipulation means i.e. during manipulation of an instrument. However, in other embodiments the instrument may be manipulated before and/or after fluid is supplied to the interior thereof. In accordance with the invention in which the instrument comprises an operation e.g. actuation or articulation transmission arrangement, the arrangement may be located in an internal passageway of the instrument. In such embodiments, it is desirable to provide relative movement between parts of the transmission arrangement and to provide internal flushing of the instrument. This may provide more thorough cleaning of the internal mechanism.

The apparatus may comprise means for supplying a flow of fluid to the interior of the instrument to be decontaminated, whether or not this is activated at the same time as manipulation of instruments, and the method may comprise providing such a flow. By irrigating the surface using a pressurised stream in this way, debris loosened e.g. by the ultrasonic waves may be more effectively flushed out of the instrument. Most preferably the flow is a pulsed flow, such that the flow includes still and moving pockets of fluid, rather than being of a constant pressure. The frequency of the pulses of fluid may vary depending upon the particular application. However, a frequency of less than 300 Hz has been found to provide a good decontamination effect, and most preferably the frequency is around 25 to around 100 Hz. A suitable pulsed flow may be obtained using a piston pump or valve system. The fluid flow may be arranged to be intermittently operated. Intermittent operation is advantageous at least while the instrument is in an ultrasonic reservoir, if present. By operating the flow only intermittently in this way, there will be periods during which the fluid within an instrument is substantially at rest, allowing ultrasonic waves to more easily penetrate the fluid along the length of the instrument and loosen debris from the interior surfaces. However, pulsed flow may be used in a deluge decontamination region alternatively or additionally to an ultrasonic decontamination region.

The frequency and time for which the flow is operated will depend upon the particular application. However, it has been found that good results may be obtained by operating the flow for around 15 seconds, and then switching it off for around 45 seconds while the instrument is in the reservoir. If desired, the ultrasonic waves may be switched off during the irrigation part of each cycle, but for ease of operation, the ultrasonic waves are preferably applied continuously. Further details of such arrangements are found in the aforementioned EP 0822 869B1. By "intermittent pulsed flow", it is meant that the flow is a pulsed flow which is switched off for certain periods e.g. while the instrument is immersed in an ultrasonic reservoir. In other words a flow is supplied to the interior of the instrument at intervals separated by periods of deadtime. The flow is pulsed in that it contains still and moving pockets of fluid, rather than being of constant pressure.

Instruments may be mounted in any appropriate manner for decontamination, provided that a portion of the instrument, and, in embodiments, only a portion of the instrument, engages the engaging means of the instrument manipulation means. The portion that engages the engaging means may be continuous or discontinuous. For example, it may be made up of a plurality of movable parts that are engaged to impart motion thereto for providing relative motion between the parts and other parts of the instrument. The apparatus may comprise means for mounting an instrument relative to the instrument manipulation means. Mounting attachments may be provided for different types of instrument. An instrument manipulation means may comprise means for mounting an instrument such that it engages the engagement means for transmitting motion thereto.

In some embodiments the decontamination apparatus comprises a removable instrument carrier located in the decontamination chamber in which instruments are placed for decontamination. The carrier is removable from the chamber for loading and unloading of instruments. The apparatus may comprise means for conveying the carrier between different parts of the apparatus or chamber. For example the conveying means may be arranged to convey the carrier such that at least a portion thereof is moved between different decontamination regions e.g. a deluge and ultrasonic decontamination region. The conveying means may be arranged such that at least a lower part of the carrier is movable between a deluge decontamination region and an ultrasonic decontamination region located therebelow.

The carrier may comprise the fluid delivery system for delivering decontaminating fluid to instruments therein, or at least a part thereof. The carrier may comprise at least a part of a fluid supply system for supplying fluid to the fluid delivery system. In embodiments in which the carrier is removable from the apparatus the fluid supply system of the carrier may be arranged to be placed in fluid communication with a fluid supply system of the apparatus when the carrier is inserted therein.

The decontaminating apparatus may further comprise one or more removable baskets in which instruments are placed for decontamination. The baskets may or may not be used together with a carrier, with the basket(s) being located in the carrier.

A basket, or indeed removable carrier, may comprise a connection for use in supplying fluid to the interior of instruments therein. The use of a basket and/or carrier may help to position instruments most effectively for decontamination, and maximise the surface area that is exposed for cleaning e.g. by holding instruments away from the edges of the decontaminating chamber.

The method of the present invention may comprise mounting the instrument in an instrument carrier or basket of the decontaminating apparatus for automatic manipulation. This may involve mounting the instrument such that it engages an engaging means of the instrument manipulation means. The method may further comprise connecting the instrument to a fluid port of the basket or carrier to enable fluid to be supplied to an interior of the instrument.

At least a part of, or the entirety of the instrument manipulation means may be provided on or by a carrier, basket or decontaminating chamber of the decontaminating apparatus where provided. Different parts of the means may be provided on different ones of a carrier, basket or decontaminating chamber of the apparatus.

Preferably the instrument manipulation means is removable from a decontaminating chamber of the apparatus. The manipulating means may be removable alone or together with a carrier or basket.

In some preferred embodiments the instrument manipulation means is provided as part of a removable carrier of the apparatus in which instruments to be decontaminated are placed, and/or as part of a basket in which instruments to be decontaminated are placed. These embodiments allow the means to be provided as a simple modification to an existing apparatus, without needing to change the main body of the apparatus. Where the instrument manipulation means is provided on a carrier or basket, this enables ready adaptation for cleaning of different instruments by simply replacing the carrier or basket with one for use with the instrument concerned e.g. arranged to suitably engage the instrument to result in manipulation thereof. In some embodiments the instrument manipulation means, or at least an instrument engaging means thereof, may be detachable from the basket and/or carrier. This would allow interchanging of the manipulation means without changing the basket or carrier as a whole.

Such a carrier or basket is believed to be new and advantageous in its own right. In accordance with a further aspect there is provided an instrument carrier or basket in which instruments to be decontaminated may be mounted in use for loading in a decontaminating apparatus, the instrument carrier or basket comprising:

means for automatically manipulating a medical instrument of the type having parts that are movable relative to one another when mounted in the carrier or basket in use to provide relative movement between two or more relatively movable parts of the instrument during an automated decontamination cycle when the instrument carrier or basket is located in a decontaminating apparatus and the automatic manipulation means is driven in use.

The instrument manipulation means may comprise any or all of the features described by reference to the decontaminating apparatus earlier. The further invention in this aspect may include any or all of the features described in relation to the other aspects or embodiments of the invention to the extent that they are not inconsistent.

A method of using the carrier or basket may comprise mounting an instrument in the carrier or basket and inserting the carrier or basket in a decontaminating apparatus in a manner such that the means for automatically manipulating a medical instrument manipulates the instrument to provide relative movement between two or more relatively movable parts of the instrument during an automated decontamination cycle of the decontaminating apparatus.

In accordance with the invention in any of its aspects or embodiments of the invention the instrument manipulation means may be a mechanical mechanism, and preferably is not electronically operated. The mechanism is preferably solely mechanical.

The decontaminating apparatus of any of the aspects or embodiments may comprise one or means for manipulating a medical instrument in accordance with any of the aspects or embodiments described herein.

The or each instrument manipulation means may be arranged to manipulate a single instrument or a plurality of instruments. Where the means is arranged to manipulate a plurality of instruments, the means may be arranged to manipulate a plurality of instruments simultaneously. In some embodiments a plurality of manipulation means may be provided in accordance with any of the embodiments described herein, each being arranged to manipulate one or more medical instruments. Different manipulation means might be used for different types of instrument. Accordingly, the methods of the present invention may involve manipulating one or more medical instruments, and may comprise manipulating a plurality of instruments simultaneously.

Preferably the apparatus is for decontaminating a plurality of medical instruments simultaneously i.e. during the decontamination cycle, and the method comprises such a step. The instruments may all be located in the decontaminating chamber. The method may comprise manipulating each instrument to provide relative movement between parts thereof, e.g. simultaneously. Each instrument may be of the construction described in respect of any of the aspects or embodiments above. Each instrument may be of the same or different construction. In embodiments in which a plurality of medical instruments, each having parts that may move relative to one another, are decontaminated, the apparatus may comprise one or more instrument manipulation means, each means being arranged to engage one or more of the medical instruments for transmitting motion thereto during a decontamination cycle in accordance with any of the aspects or embodiments described herein. The method may comprise using the or each instrument manipulation means to cause relative motion between parts of a respective set of one or more medical instruments. The or each instrument manipulation means may be arranged to engage one or more medical instruments having parts that may move relative to one another.

It will be appreciated that while the apparatus described herein in accordance with the invention in any of its aspects or embodiments is adapted for the decontamination of a medical instrument of the type having parts that may be moved relative to one another in use, the apparatus may (simultaneously) be used to decontaminate instruments of a different construction i.e. instruments without moving parts. In embodiments the apparatus is arranged to provide automatic manipulation of each of a first set of medical instruments in the decontaminating apparatus during a decontamination cycle, each instrument of the first set having parts that are movable relative to one another, and to simultaneously provide decontamination of a second set of one or more instruments without automatic manipulation of the instruments. The second set of instruments may comprise instruments that do or do not have parts movable relative to one another. The instruments that are not manipulated may be instruments that do not have relatively movable parts or could be instruments having parts movable relative to one another are not to be manipulated during decontamination for any reason. The method may comprise manipulating each of a first set of medical instruments during the decontamination cycle, each instrument of the first set relatively movable parts, and simultaneously decontaminating a second set of one or more instruments in the decontamination apparatus without manipulation of the instruments.

In embodiments, medical instruments may be located in the apparatus appropriately depending upon whether manipulation is required during the decontamination cycle. Instruments to be articulated may be located appropriately with respect to the means for manipulating instruments, while other instruments may be located in other parts of the apparatus away from the means. In embodiments, the decontamination region of the apparatus and/or a removable carrier thereof may comprise a first region for decontaminating medical instruments having relatively movable parts, the first region comprising the means for manipulating instruments, and a second region for decontaminating medical instruments that do not require manipulation during the decontamination cycle. The method may comprise mounting a set of one or more medical instruments having relatively movable parts to be manipulated during decontamination in the first region, and mounting one or more medical instruments that do not require manipulation during decontamination in the second region. These instruments that do not require manipulation may or may not have relatively movable parts. The first region may be a lower region of the apparatus or carrier. In some embodiments the regions of the apparatus may be provided by regions of a carrier located therein.

BRIEF DESCRIPTION OF THE DRAWINGS

Some preferred embodiments of the invention will now be illustrated by way of example only and by reference to the following drawings of which;

FIG. 2 is a schematic view of an instrument carrier incorporating an instrument manipulation means in accordance with one embodiment of the invention:

FIG. 3 illustrates an instrument manipulation means and driving means in accordance with a first embodiment of the invention:

FIG. 4 illustrates an instrument manipulation means and driving means in accordance with a second embodiment of the invention;

FIG. 6D illustrates a manipulation means in accordance with a further embodiment for use with the device shown in FIGS. 6 A, B and C;

FIG. 7A illustrates an underside of a movable plate of a further type of interface of a robotic instrument that the manipulation means may cooperate with in a further embodiment;

FIG. 7B is a view of the plate of FIG. 7A from above showing the way in which it may move relative to other parts of the interface in use;

FIG. 7C illustrates another embodiment of an instrument manipulation means that may be used with an instrument having an interface with a movable plate as shown in FIGS. 7A and B;

DETAILED DESCRIPTION

Figure 1:
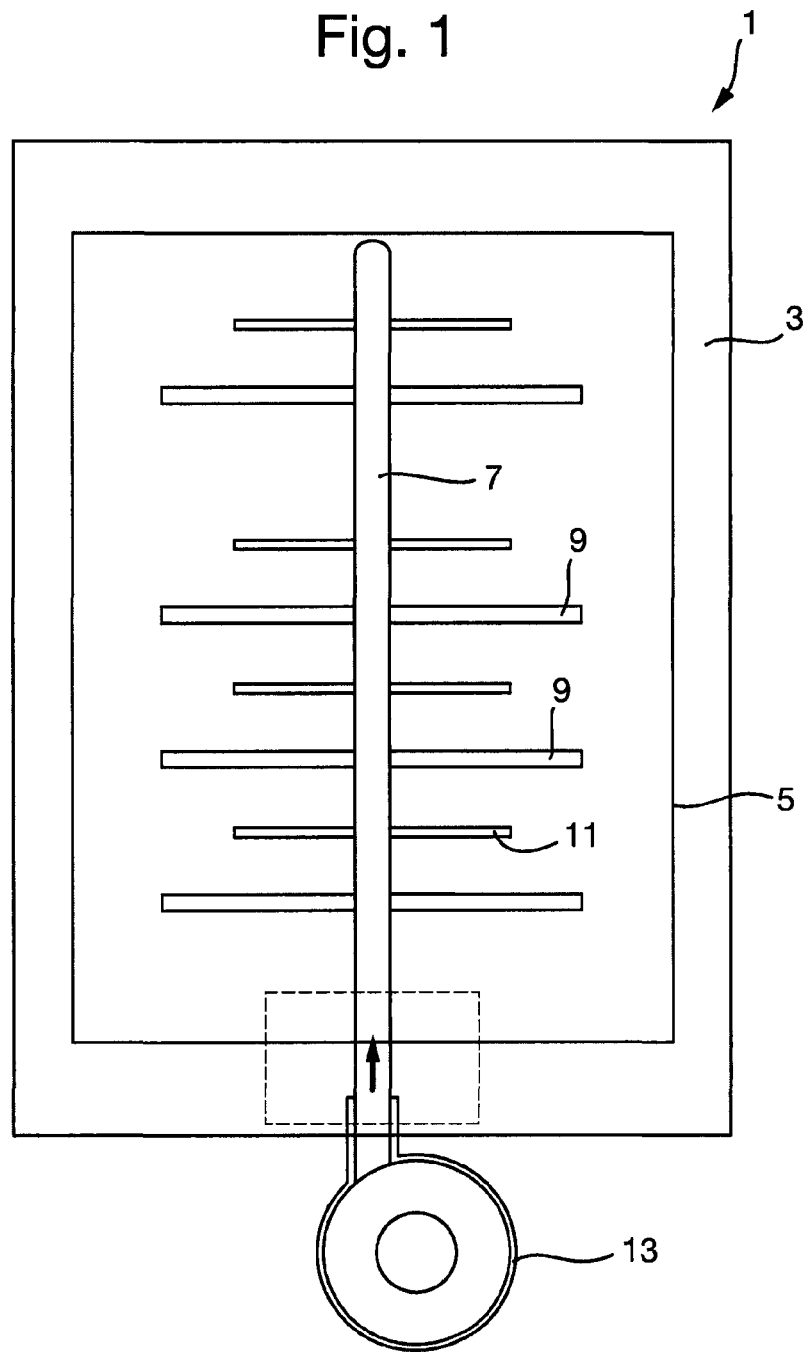
FIG. 1 is a schematic vertical cross sectional view of a decontaminating apparatus with which the instrument manipulation arrangement of the present invention may be used.

FIG. 1 is a vertical cross sectional view of a decontaminating apparatus with which the instrument manipulation arrangement of the present invention may be used. The decontaminating apparatus shown in FIG. 1 is a conventional cabinet style washer, arranged to provide deluge decontamination of medical instruments when located therein. The washer includes a main housing defining a wash chamber 3. A removable instrument carrier 5 is mounted within the wash chamber. In use, the instruments to be decontaminated are mounted in the carrier. The carrier may be inserted in or removed from the wash chamber for loading or unloading of instruments as known in the art. The instrument carrier 5 includes various shelves upon which instruments to be cleaned may be placed, either directly, or by placing the instruments first in baskets. The shelves are not shown in FIG. 1 for simplicity.

The carrier defines a central column 7 defining a main fluid passageway through which the decontamination fluid may flow in use. A lower end of the column is in fluid communication with an outlet of pump 13. The lower end of the column is fluidly connected to the outlet of the pump when the carrier is inserted in the wash chamber, and is disconnecteable therefrom to permit removal of the carrier from the chamber. The connection is within the region of the dotted lines. The pump 13 is located in the base of the apparatus, and provides a flow of decontaminating fluid in use in the direction indicated by the arrow in FIG. 1.

A plurality of spray arms 9, 11 extend perpendicular to the column 7 and each define a fluid flow path extending along the length thereof in fluid communication with the main flow path of column 7. The arms comprise fluid outlets along the lower sides thereof for providing fluid in the form of a spray to the interior of the wash chamber in use. The spray arms include the longer spray arms 9 and shorter spray arms 11, although it will appreciated that other configurations of spray arms may be used. For example, shorter spray arms 11 may be omitted.

Decontaminating fluid will pass upwards through the fluid path defined by column 7 in use, and will exit the column via fluid paths defined by the plurality of spray arms 9, 11 to be discharged in the form of droplets through the outlets of the spray arms. The spray arms 9, 11 are arranged to be hydraulically actuated to rotate around the central column 7 when fluid is pumped through the fluid path of the central column and from there along the fluid paths spray arms to provide a spray for decontaminating the external surfaces of instruments located in the carrier in use. This is a conventional deluge decontamination type arrangement, similar to that employed in dishwashers.

In some arrangements, the instrument carrier 5 may be inserted into the wash chamber 3 at a first vertical level. The wash chamber may comprise a conveying system, which is not shown in FIG. 1, to enable the instrument carrier to then be lowered toward the base of the chamber to enable the central column 7 to be located in fluid communication with the outlet of the pump 13 to enable fluid to be pumped upward to the column in use.

While the apparatus shown in FIG. 1 specifically illustrates a deluge decontamination apparatus 1, the invention is applicable to decontamination apparatus which additionally or alternatively is arranged to carry out ultrasonic decontamination of instruments. In a combined ultrasonic/deluge decontamination apparatus, the lower part of the wash chamber of the type shown in FIG. 1 may be filled with fluid, to cover instruments located at lower levels of the carrier. The apparatus may comprise suitable ultrasonic transducers for applying ultrasonic waves to the instruments which are immersed in the fluid during the relevant part of the decontamination cycle. The lower part of the wash chamber may then be drained so that the same instruments can undergo deluge decontamination. In other arrangements, an instrument carrier might be conveyed towards a lower part of the apparatus for immersion of instruments in a reservoir defined in the base thereof for ultrasonic decontamination, and then raised to remove the instruments from the reservoir as a appropriate in a decontamination cycle.

The decontamination apparatus 1 of FIG. 1 is configured to perform an automatic decontamination cycle in use.

In yet other arrangements, the decontamination apparatus may simply be an ultrasonic decontamination apparatus without deluge decontamination means. Such an apparatus might be in the form of an ultrasonic bath into with instruments can be placed e.g. by mounting them first in a basket. Such an apparatus may be a chest style washer.

Referring now to FIG. 2, a carrier system for use in a deluge decontamination apparatus of the type shown in FIG. 1 is illustrated. This carrier would be used in the place of carrier 5 illustrated in FIG. 1, and incorporates the modification of the present invention. It also differs slightly in the spray arm configuration. As with the carrier of FIG. 1, the carrier of FIG. 2 includes spray arms 22 arranged to rotate about a vertically extending central column 26. In use, the carrier is inserted into a decontamination chamber of a decontamination apparatus of the type shown in FIG. 1, and the lower most end of the central column 26 placed in fluid communication with a pump for pumping decontaminating fluid upwards through the flow path defined by central column and then through the flow paths of spray arms for delivery to instruments located in the chamber in use as described by reference to FIG. 1. The carrier includes shelves 24 at different vertical levels. In the arrangements shown, the shelves are configured so that instruments can be directly placed on the lowermost shelf 24 for decontaminating. However in other arrangements instruments might first be placed in instrument baskets.

The carrier shown in FIG. 2 additionally includes fluid paths in peripheral columns 28 extending vertically at the sides of the carrier. These are located on either side of the central column 26, and are likewise connected to the fluid supply means of the decontaminating apparatus when the carrier is located therein, so that fluid may additionally be caused to flow along these peripheral paths. Fluid may be caused to flow along either the peripheral or central flow path, or along both, under the control of a processor controlling operation of a decontaminating cycle of the apparatus when the carrier is located in an apparatus in use. Fluid from the peripheral paths is able to flow to the flushing attachments 30, which are shown as being spaced at intervals along one side of the shelf at the lowest level of the carrier. Similar attachments may be provided on the opposite side of the shelf. Suitable fluid paths may be used to achieve flow of fluid from the peripheral columns into the arms of the rack. In use, instruments may be connected to the flushing attachments 30 so as to allow fluid to be pumped via the flushing attachments 30 into the interior of the instruments for internal cleaning.

The modification of the carrier in accordance with the invention will now be described. As illustrated schematically in FIG. 2, the instrument carrier has been modified to provide an instrument manipulation arrangement 40 having instrument engaging means 52. The instrument manipulation means is shown in solid shading. An arrangement for interacting with fluid flowing along the flow path defined by central column 26 in use to hydraulically drive the arrangement is connected to an end of the instrument manipulation means 40 remote from an end at which instrument engaging means 52 is located. Of course, the arrangement could alternatively be located to interact with one of the peripheral flow paths defined by columns 28. In the example shown in FIG. 2, the arrangement for interacting with a flow path is a water wheel device 42.

A suitable intermediate arrangement of mechanical linkages and/or gears schematically illustrated by block 44 connects the water wheel 42 to a shaft 46 so as to result in suitable rotation of the shaft for use in providing motion that is transmitted to an instrument via the instrument engagement means 52. In the illustrated arrangement the shaft 46 extends horizontally to a mechanical linkage 48, which connects it to a further shaft 50 which extends vertically up one of the peripheral arms 28 of the apparatus. A further mechanical linkage 51 is provided at the end of shaft 50 to connect the shaft 50 to the instrument engaging means 52 on either side thereof.

The rotation of the shaft 46 provides movement which may be transmitted via the intermediate arrangement to instrument engaging means 52 associated with the lower shelf 24, for transmitting motion appropriately to instruments mounted on the shelf in engagement with the engaging means 52. In the arrangement shown, two sets of instrument engaging means are provided on each side of the peripheral column 28 for interaction with different instruments mounted in the carrier.

While FIG. 2 illustrates one possible intermediate arrangement, it will be appreciated that any suitable arrangement may be provided between the driving means and the instrument engagement means of the instrument manipulation means to provide suitable movement to the instrument engagement means 52 for transmittal to instruments engaged therewith. This would depend e.g. upon the desired direction of motion, type of movement, e.g. whether linear, reciprocating, rotational etc, as well as the position of the instrument engaging means relative to the driving means etc.

Some exemplary arrangements of the instrument engaging means 52 for use of different types of instruments will be described later, as well as some alternative intermediate arrangements by which motion imparted to a rotary shaft used in providing the motion that is transmitted to instruments.

While the instrument manipulation means 40 has been shown as being a part of the instrument carrier 20 in FIG. 2, it will be appreciated that this is not essential. For example, the instrument manipulation means might be provided as part of the wash chamber of a washer such as in FIG. 1, or alternatively of an ultrasonic bath-type washer apparatus. In other arrangements the instrument manipulation means might be provided as part of a basket which is inserted into the wash chamber, either directly, or after being mounted in a carrier, in use. Such baskets include flow paths e.g. for supplying fluid to the inside of instruments located therein which be harnessed to provide a suitable hydraulic source of power for the instrument manipulation means.

Arrangements in which the manipulating means is provided as part of a removable basket or carrier of the apparatus allow simple changing between manipulating means for use with different instruments by selecting the carrier or basket appropriately.

In yet other arrangements, the instrument manipulation means might be provided in part by more than one component of a decontaminating apparatus e.g. by any one or ones of a wash chamber, instrument carrier, instrument basket, or other component of a washer.

The manipulating means might be arranged to be detachable from the carrier or basket. The instrument manipulation means might similarly be arranged to be detachably connected to a wall of the wash chamber. Where means is provided for interacting with a fluid flow path for hydraulically powering the arrangement, the manipulation means might be detachable therefrom to enable removal of the manipulation means from the basket, carrier or wash chamber.

While a hydraulic driven arrangement of the instrument manipulation means 40 is illustrated in FIG. 2, and the exemplary embodiments herein, it will be appreciated that it is not necessary for the arrangement to be hydraulically driven, and in addition, or alternatively, other sources of power may be used. For example, a magnetically driven arrangement may be used, by means of a magnetic coupling through the walls of the wash chamber. Typically such walls may be made of stainless steel, which provides the ability for such magnetic coupling arrangements to be used. Magnetic or hydraulic coupling arrangements are particularly suitable for use with wet decontaminating systems, as they present no complication of electronic parts needing to be sealed from fluid in the interior of the wash chamber. However, electrically driven arrangements may also be used, using a suitable coupling through a wall of the wash chamber, e.g. to an electric motor. In these arrangements, appropriate fluid sealing between the internal and external parts of the arrangement would be required. Hydraulically driven arrangements are preferred in that they can simply harness a pre-existing flow in the wash chamber, and may be achieved with minimal adaptation of existing arrangements.

In yet other arrangements, the ultrasonic energy of ultrasonic waves produced for use in the ultrasonic decontamination of instruments, where the apparatus is arranged to provide ultrasonic decontamination, may be used in driving the instrument manipulation means. One or more ultrasonic wave source, such as a piezoelectric transducer, may be located externally to or within an ultrasonic reservoir of the wash chamber, which causes ultrasonic waves to propagate within the reservoir for the ultrasonic decontamination of instruments. Ultrasonic waves produced within the reservoir may drive one or more transducer e.g. located within the reservoir, such as a piezoelectric transducer, which in turn drives the instrument manipulation means e.g. via one or more servomotors. As the ultrasonic drive arrangement requires no electrical or mechanical connection with components external to the decontamination chamber e.g. via wires, the drive mechanism including a piezoelectric transducer and servomotors may be mounted within a sealed unit within the decontamination chamber without the need for modifying the wall of the chamber to create an opening therethrough.

With reference to FIGS. 3 to 9 some exemplary embodiments of instrument manipulation means in accordance with the invention will now be discussed.

FIG. 3 illustrates a simple form of instrument manipulation means. The instrument manipulation means 54 comprises a proximal end connected to a water wheel 56. The water wheel 56 is located in a fluid flow path 58 of a decontaminating apparatus of the type that has previously been described by reference to FIG. 2. In other arrangements, the water wheel 54 might instead be replaced by a part of a magnetic or electrical coupling for driving the shaft 57.

The water wheel 56 is located at a proximal end of a shaft 57. In use, fluid flow in the direction of the arrow along the flow path 58 will cause rotation of the water wheel, and hence rotation of the shaft 57. At the opposite or distal end of the shaft 57, instrument engaging means 53 comprising an engaging element in the form of a pin 59 is provided for transmitting motion to instruments to create relative motion between parts thereof. The arrangement includes a cam 55 which is arranged to rotate with the shaft 57 upon which the pin 59 is mounted to impart it with circular motion. The engagement pin 59 provides an engaging element defining a plurality of surfaces which engage with a part of an instrument to impart motion thereto. As will be described in more detail below, in the illustrated arrangements, the pin 59 is configured to mate with a moveable wheel in an interface at the hub of an articulation transmission arrangement of a robotic instrument.

Although not shown in FIG. 3 for simplicity, any suitable form of mechanical linkage and/or gearing might be provided between the water wheel 56 and the rotary shaft 57.

FIG. 4 illustrates an alternative more complex arrangement which may be used to provide appropriate movement of an instrument engaging element in the form of a pin for transmission to an instrument in a similar manner to that of FIG. 3. In this arrangement, corresponding parts of the apparatus are given a similar reference numeral to those of FIG. 3, but preceded by "6" rather than "5". Thus, the instrument manipulation means 64 includes a water wheel 66 located in a fluid flow path 68, for causing rotation of a shaft 67. The instrument engaging means 63 includes an instrument engaging element 69 in the form of a pin, connected to a rotary cam 65.

In contrast to the FIG. 3 arrangement, in this arrangement, an additional linkage 62 is provided for transmitting motion of the rotary shaft 67 to a further shaft 61 perpendicular thereto so that rotation of the engagement pin 69 occurs about a vertical axis rather than a horizontal axis.

It will be appreciated that this type of intermediate arrangement, or any other suitable intermediate arrangement may be provided between a driven part of the manipulation means e.g. a driven shaft and the instrument engagement means to ensure that the movement of the instrument engagement means e.g. elements occurs in an appropriate direction, and is of an appropriate form for transmission to an instrument, depending upon how the instrument is to be mounted in the decontaminating apparatus, and the type of mechanism of the instrument with which the manipulating means is to interact.

Although the arrangements shown involve rotation of an instrument engaging element, and of a drive shaft for providing motion that can used in providing the motion that is transmitted to instruments via the instrument engaging means, it will be appreciated that other types of motion may be used. For example, reciprocating or linear motion may be imparted to a driven part of the manipulation means, or to an engagement means thereof.

Figure 5:
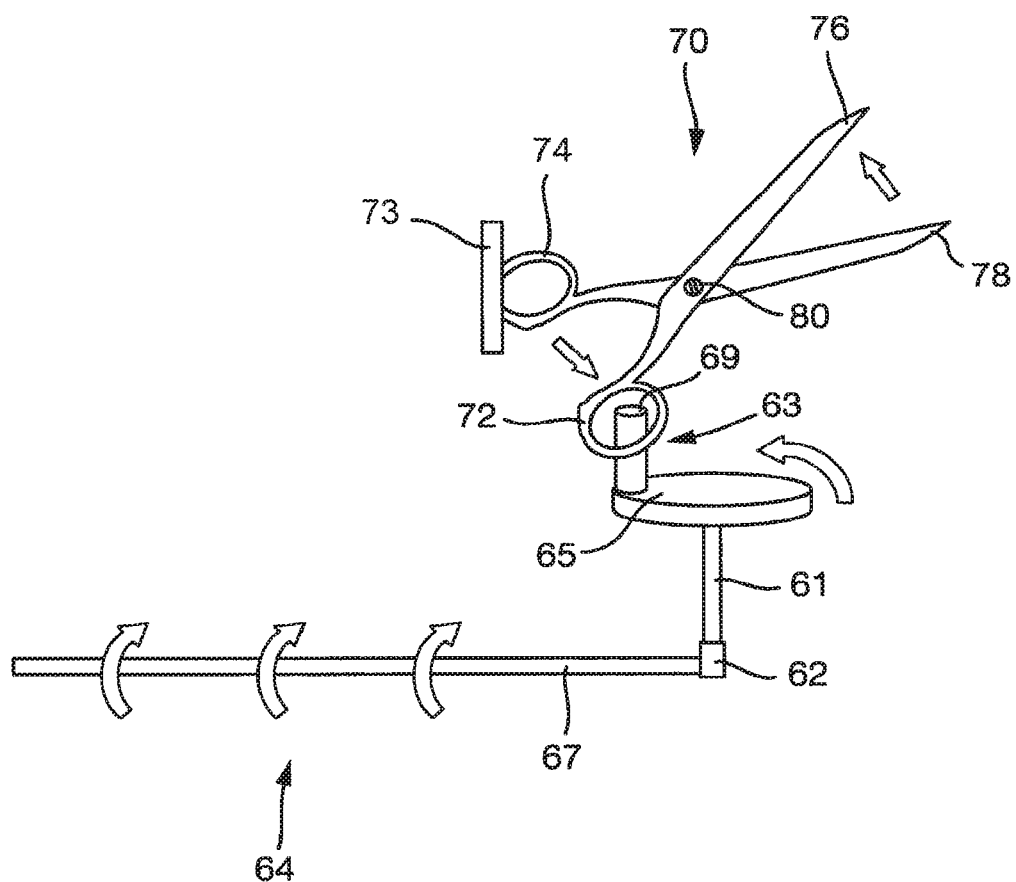
FIG. 5 illustrates the use of the embodiment of FIG. 4 to manipulate scissors.

Referring now to FIG. 5, an example of the way in which an arrangement of type shown in FIG. 4 might be used to create relative movement between parts of an instrument to be manipulated is shown. The instrument manipulation means in FIG. 5 corresponds to that shown in FIG. 4, although the water wheel and flow path are not shown at the proximal end thereof for simplicity. In this arrangement it can be seen that a pair of scissors 70 is arranged with the engagement pin 69 located through one of the handles 72 i.e. finger holes of the scissors. The other handle or finger hole 74 is attached to a fixed point 73, such as a point of the carrier, or which could be provided as part of the instrument manipulation means.

As the shaft 67 rotates, the cam wheel 65 rotates about a vertical axis causing circular movement of the pin 69. In this way, relative movement is created between the parts of the operating portion i.e. handles of the scissors, to thereby result in actuation at the distal end of the scissors as the distal tips 76,78 of the scissors move relative to one another. In addition relative movement is indirectly provided between parts of the scissors at the pivot joint 80. As the engagement pin 69 rotates, the scissors will be caused to alternatively open and close with corresponding relative movement of the parts at the operating portion and joint.

In this way, it will be appreciated that the present invention provides relative movement between a first set of parts of the instrument, in this case scissors, by engaging with a first set of relatively movable parts i.e. the operating handles 72,74, which relative movement results in further relative movement between the remotely located distal tips 76,78 of the scissors, and at the joint 80. In this way, the full range of movement of the scissors may be achieved during decontamination cycle, exposing surfaces at the operating end or handle portion, the distal working end, and also of the pivot joint 80 to the decontaminating process.

Turning to FIG. 6, the way in which an instrument manipulation means of the present invention may be used to manipulate more complex instruments during decontamination will be described.

Figure 6A:
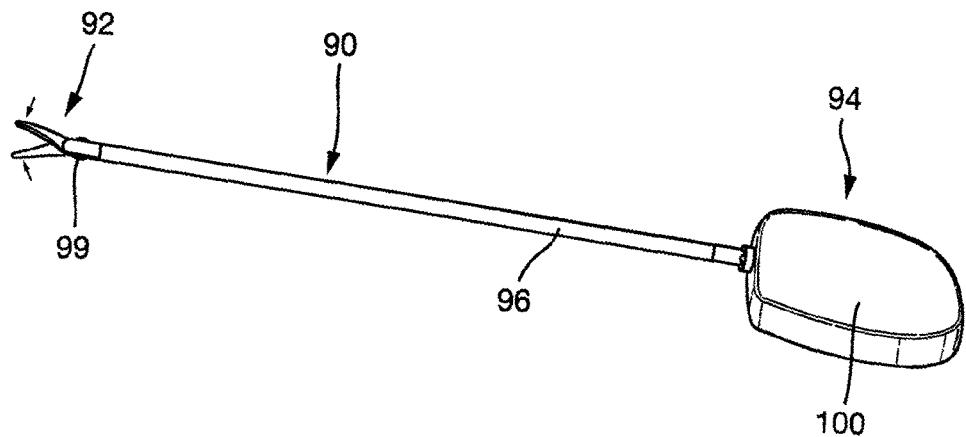
FIG. 6A illustrates a robotic surgical device that may be manipulated.

FIG. 6A illustrates an instrument of the type which is to be manipulated. The instrument is a robotic surgical instrument 90, having a proximal end 94 for connection to a robotic manipulation arm, and a distal end 92 defining a working portion in the form of an end effector 92, being a pair of scissors, for interaction with the body in use. The end effector 92 is connected to the distal end of a shaft 96 of the instrument by means of a wrist 99 to allow articulation of the end effector about the end of the shaft in various manners. For example, this may be arranged such that the end effector has five or even seven degrees of freedom. At the proximal end of the shaft the instrument includes a hub 100 by means of which the instrument is connected to the distal end of a robotic manipulator arm in use. The underside of the hub 100 defines an operation interface by means of which interface the hub 100 is matingly connected to the robotic arm in use. The robotic arm will interact with the interface in use to remotely control articulation of the end effector 92 at the distal end of the instrument, and to control relative movement of the parts of the end effector e.g. to move the blades of the scissors relative to one another via a transmission mechanism comprising cables extending along the shaft 96 between the hub 100 and the effector 92. The robotic arm does this by providing a suitable input to the operation interface ultimately based on an input provided by a surgeon.

Figure 6B:
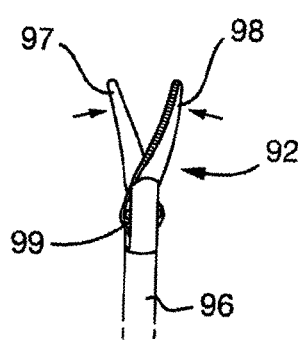
FIG. 6B illustrates a working portion of the device.

FIG. 6B shows the distal end of the instrument in more detail, illustrating that the end effector i.e. scissors include blades 97 and 98 that are movable toward one another as shown. The end effector 92 is also articulatable about wrist 99 relative to the distal end of shaft 96 to control the angle of the blades.

Figure 6C:
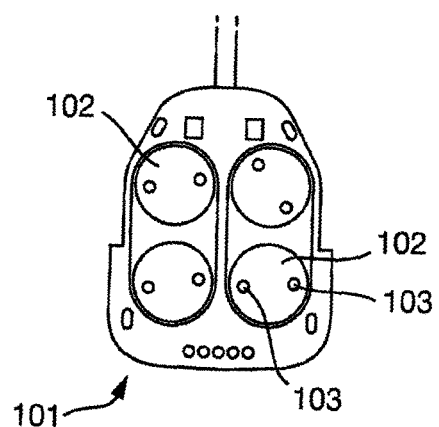
FIG. 6C illustrates an operation interface of a hub of the device for connection to a robotic manipulator.

FIG. 6C shows the interface 101. The interface 101 includes a plurality of control dials 102 which are rotatable under the control of the robotic arm, and are connected via cables of the actuation transmission mechanism (not shown) to parts of the wrist 99 and/or end effector 92 at the distal end of the instrument to enable remote control of articulation of the end effector e.g. scissors 92. It will be seen that each movable dial 102 defines sockets 103 for receiving pins of a robotic manipulator arm to enable rotation of the dials to be carried out under the control of the robotic arm. In this way, articulation may be controlled as appropriate by the robotic arm under the control of a surgeon. A robotic arm might be controlled e.g. by a computer program, or directly e.g. by an input means such as a joystick operated by a surgeon.

Turning now to FIG. 6D, a suitable instrument engaging means 110 is illustrated for manipulation of this type of instrument. In a similar manner to the embodiment shown in FIG. 4, the arrangement includes instrument engaging elements 115 in the form of pins. In this case the engaging means 110 includes a plurality of instrument engaging elements 115, each mounted to a rotary cam 113 to provide circular motion of the respective pin in use. The cams 113 are connected an intermediate mechanical arrangement including peripheral shafts 117 and linkages 118 to a main shaft 119 which is driven so as to rotate e.g. as shown in FIG. 4. The mechanical arrangement is such that the cams 113 rotate about a vertical axis to result in circular movement of the pins 115. In this case, four engaging elements 115 are provided for interacting with each of the dials 102 of the actuation transmission interface 101.

In use, the instrument 90 is mounted in the carrier relative to the engagement means of the instrument manipulation means so that one of the sockets 103 of each of the movable dials 102 is in mating connection with one of the pins 115 of the instrument manipulation arrangement. When the instrument manipulation arrangement is operated, the pins 115 rotate with a circular motion causing rotation of the movable control dials 102 of the interface. This results in relative movement between the blades 97 and 98 of the end effector 92 of the instrument, and of the parts of the actuation transmission mechanism.

Depending upon the way in which the movable dials are moved, and which dials are moved, articulation of the end effector 92 through each of a possible range of movements about the wrist 99 may be achieved. In this way, thorough cleaning of the end effector 92 and the wrist 99 may be achieved. At the same time thorough cleaning of the relatively parts of the interface may be achieved, and, where internal flushing is implemented, of the parts of the articulation transmission arrangement connecting the movable dials 102 to the end effector 92.

FIGS. 7A-C illustrate yet another arrangement by which manipulation of an instrument may be achieved. This arrangement is suitable for use with a robotic type instrument having an operation interface comprising a movable plate. Such a plate is shown from the underside in FIG. 7A. The remainder of the interface, e.g. a base relative to which the plate moves, is not shown. The plate is arranged to be pivotable about a centrepoint to impart it with motion of the type illustrated in FIG. 7B in use, and therefore acts as a "wobble plate". Movement of the plate in different manners will act as an input to control remotely the manner in which a working portion of the instrument is actuated via an actuation transmission mechanism, such as a plurality of cables. In other words, the plate might be an alternative to the arrangement used in the actuation interface of FIG. 6b, which includes movable parts in the form of rotatable dials which are movable relative to a base of the interface to indicate a desired actuation.

Referring to FIG. 7C, the instrument manipulation means 120 is similar to that of FIG. 4, and includes a shaft 124 which is driven by a water wheel 122 in use. The shaft 124 is connected by a linkage 126 to a peripheral shaft 128. An instrument engaging arrangement 130 includes an instrument engaging element in the form of ball 136 mounted on a pin 134, which in turn is mounted to the periphery of rotary cam 134 to provide it with circular motion. The surface of the ball 136 engages the underside of plate 200 at the recess 208 at its periphery as shown schematically in FIG. 7C. A further pin 138 is provided with a ball 140 on the top thereof, and is mounted to the centre of rotary cam 132 so as to rotate about its axis in use. The ball 140 engages the recess 210 in the centre on the underside of plate 200 to support the plate. In this way, movement of the plate is caused relative to a remainder of the operating interface to which it is mounted as the pin 134 moves in a circular path to cause movement around the periphery of the plate in a vertical plane as shown in FIG. 7B, to expose different surfaces of the plate, and interface for decontamination. The plate itself does not rotate. In addition, movement of the plate will actuate the working portion of the instrument causing relative movement between parts thereof, and also will result in relative movement between parts of the actuation transmission to ensure more thorough cleaning as described by reference to FIGS. 6A-D.

Figure 8:
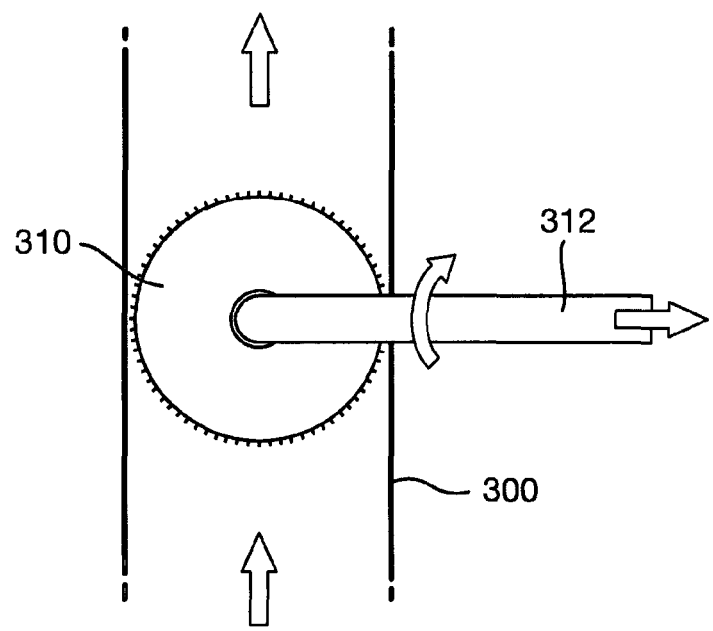
FIG. 8 illustrates a driving arrangement for the manipulating means in accordance with one embodiment in more detail.

FIG. 8 illustrates in more detail a possible arrangement for hydraulic driving of an instrument manipulation means. In this arrangement water wheel 310 is located in flow path 300. Flow of fluid along the path in the direction shown results in rotation of the water wheel 310, and corresponding rotation of the drive shaft 312 connected thereto. This shaft may be connected to a suitable mechanical linkage, and ultimately to an instrument engaging means of an instrument manipulation means as described earlier.

Figure 9:
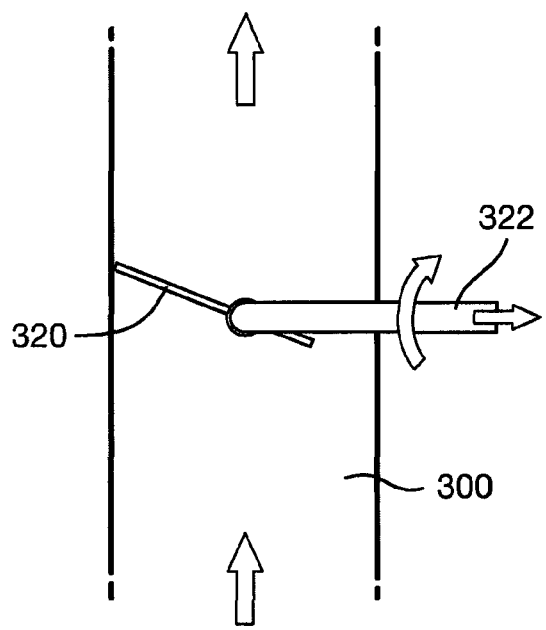
FIG. 9 illustrates an alternative driving arrangement that may be used in accordance with the invention.

FIG. 9 illustrates an alternative arrangement, where, rather than using a waterwheel, a butterfly valve 320 is provided in the flow path 300 and connected to rotational shaft 322. This will provide a semi-rotational movement of the shaft when fluid flows along the fluid flow path 300, which may be used in providing the motion that is transmitted via instrument engaging means of the instrument manipulation means to an instrument in use in a similar manner to arrangements using a waterwheel.

Operation of the invention will now be described. Referring to FIG. 2, instruments to be decontaminated are mounted appropriately with respect to the carrier. A carrier having the appropriate engagement means for the type of instrument to be cleaned is chosen. The instruments may be located directly on the shelves, or first located in baskets which are then located on the shelves. If internal flushing is to be provided, flush ports of the instruments are connected via means of flexible conduits to the flushing attachments 30. The instruments are located with respect to the engagement means in a manner such that the moveable parts of their operating mechanism are suitably engaged with the engaging elements of the instrument engaging means for transmitting motion thereto.

For instrument engaging means of the type shown in FIG. 5, an instrument in the form of scissors is located such that one finger hole of a handle is located over an instrument engaging pin of the instrument engaging means, and the finger hole of the other handle is attached to a fixed part of the carrier.

Where the instrument engaging means is of the type shown in FIG. 6D for engagement with the operating dials of an operating interface of a robotic instrument as shown in FIG. 6A, pins 112 of the instrument engaging elements are arranged to mate with the recesses 103 in the dials 102.

In other arrangements as shown, for example in FIG. 7C, balls 136 of the instrument engaging means are arranged to mate with co-operating recesses of a plate of the instrument operation interface.

The instrument carrier is then located in the wash chamber of the decontaminating apparatus. The instrument carrier is appropriately located in fluid communication with fluid supply means of the apparatus so that decontaminating fluid may be supplied via the central and peripheral flow paths to the spray arms 22, flushing attachments 30, and also to the water wheel 42 for driving the instrument manipulation means 40.

A decontamination cycle may be implemented in the usual manner. The instrument manipulation means may be controlled to be activated at any particular stage or stages of the decontamination cycle. The available stages will depend upon the type of apparatus. The instrument manipulation means may be activated during deluge and/or ultrasonic decontamination or soaking of instruments without ultrasonic cleaning, or before or after such stages if available. The manipulation may or may not be activated simultaneously with energising of the ultrasonic transducers during ultrasonic cleaning, as movement of instruments may interfere with development of ultrasonic waves in the ultrasonic bath. However, this may already be impacted by the operation of deluge decontamination means, and in practice the additional operation of manipulation means during deluge decontamination means operation while some instruments are undergoing ultrasonic cleaning is envisaged.

The decontamination fluid used may be water, or may include disinfecting agents or other cleaning agents. The composition of the decontaminating fluid may vary at different times in a decontamination cycle under the control of a microprocessor controller.

Where internal flushing is instrumented provided, this may be achieved by pumping fluid to flushing attachments e.g. 30 as shown in FIG. 2 and thus to the interior of an instrument connected thereto directly, or via a connecting conduit. Where internal flow is provided, this may be achieved using a piston pump arranged to provide a pulsed flow of decontamination fluid. The frequency of the pulsed flow may be around 25 to 100 Hz. A pulsed flow may help for flush debris loosened by ultrasonic waves along an instrument, and out of the instrument. Alternatively, a pulsed flow may be achieved using a suitable valve arrangement associated with the fluid path supplying the internal flushing means 30, rather than using a piston pump.

Where ultrasonic decontamination is provided, the frequency of the ultrasonic waves might be for example between 20 and 40 Hz.

In combined deluge/ultrasonic apparatus, instruments may undergo one or more cycles of ultrasonic and deluge decontamination as required where both deluge and ultrasonic decontamination means are provided. By carrying out deluge decontamination after ultrasonic decontamination, loosened debris may be more effectively washed form surfaces of instruments. Instruments may then be returned to an ultrasonic decontamination region after deluge for further decontamination. A number of cycles may be carried out using decontaminating fluid at different temperatures, or using different decontaminating agents to achieve cleaning, and defined desired disinfection of instruments.

In general, a carrier may be located in the wash chamber, and lowered so that instruments of the lower shelf are located in an ultrasonic reservoir of an apparatus (where provided). The reservoir may be filled to immerse instruments which may then soak with or without the application of ultrasonic waves to the liquid at different times. Instruments at higher levels of the carrier may simultaneously undergo deluge spraying. During deluge spraying, ultrasonics are preferably not activated for the reservoir. Subsequently the reservoir may be drained or the carrier raised to allow the instruments that were immersed to undergo deluge cleaning. Internal flushing may be carried out while instruments are in the reservoir or during deluge cleaning or before or after such stages.

It will be appreciated that the decontaminating apparatus of any of the embodiments may be operated under microprocessor control to provide a number of different cycles. For example, the factors such as the temperature of the fluid emitted by deluge sprayers, sequence of pulsed flow provided to the interior of the instruments, is applicable, duration of flushing, nature of decontaminating fluid, duration and timing of activation of instrument manipulation means etc may be set as appropriate Suitable microprocessors controllers are known in the context of decontaminating washers, dishwashers and washing machines.

Activation of the instrument manipulation means at an appropriate time or times in a decontaminating cycle may be achieved by sending a flow of fluid along the main flow path in the FIG. 2 arrangement, for example. This would result in activation of the manipulating means at the same time as deluge decontamination occurs in the simple arrangement shown. Of course, an arrangement may be used to allow the manipulation means to be activated independently of the deluge decontamination means.

In one example of an automated decontamination cycle including instrument manipulation, the instrument carrier is lowered so as to immerse the instruments of the lower shelf 24, which are engaged with the instrument engaging means of the manipulation means, in a reservoir at the base of the decontamination chamber, which is used for ultrasonic decontamination. Here the instruments soak, being cleaned due to being immersed in fluid, with or without applying ultrasonic waves to the liquid. The main flow path would then be operated to commence deluge decontamination of instruments located at higher levels. This would activate the instrument manipulation means, manipulating instruments immersed in the reservoir while deluge decontamination occurred for instruments above. The ultrasonic transducers are switched off at this stage. The deluge decontamination stage is then ceased, and internal flushing carried out of the instruments which have undergone manipulation, again without application of ultrasonic waves to the reservoir.

In another example, deluge cleaning may be carried out, and at the same time, instrument manipulation of the instruments undergoing deluge cleaning. Subsequently, deluge cleaning and manipulation may cease, and internal flushing may be carried out. This cycle may not include ultrasonic cleaning and may be carried out in the main decontaminating region without needing to fill a reservoir.

In other arrangements manipulation may take place while instruments are located in an ultrasonic reservoir, preferably without the ultrasonic waves being applied to the fluid at the same time. This may be used in a combination deluge/ultrasonic apparatus, or an apparatus which only contains an ultrasonic reservoir, and not decontaminating means.

Rather than providing manipulation means as part of a carrier of an apparatus, an instrument basket may be adapted to incorporate instrument manipulation means in accordance with any of the embodiments with the invention.

The instrument basket may incorporate instrument manipulation means arranged for example along the lines that which has been added to the carrier shown in FIG. 2. Hydraulic power might be achieved by harnessing a flow path for supplying fluid to the interior of instruments located in the basket. The basket may include flushing attachments which are placed in fluid communication with fluid supply means of a carrier or decontamination chamber in use to enable fluid to be delivered via conduits attached thereto for supply to the interior of instruments.

Examples of ultrasonic decontamination machines with which the invention may be implemented include Medisafe UK Limited's Sonic Irrigator® range e.g. the Sonic Irrigator® SA®, and Sonic Irrigator® PCF®. Examples of combined deluge/ultrasonic apparatus include Medisafe UK Limited's Niagara® SA Ultrasonic® and Niagara® SA PCF® machines.

The invention is applicable to any instrument having relatively movable parts, and not just more complex surgical instruments or scissor type instruments illustrated. For example, laparoscopic and other instruments for minimally invasive procedures may be manipulated. Such instruments may include a handle portion that is operated manually via a surgeon to control manipulation of a working portion at a distal end thereof. The handle portion may be manipulated in a similar manner to scissors and may include further degrees of freedom of input devices e.g. buttons, wheels, dials etc which may be operated to indicate a particular type of manipulation which may be transmitted via a transmission arrangements e.g. comprising cables as in the robotic instruments described above.

The invention claimed is:

1. A method for decontaminating a medical instrument having parts that are movable relative to one another, the method comprising:
    providing an instrument manipulation means having an instrument engaging means engageable with the instrument,
    mounting the instrument in a decontaminating apparatus having a fluid flow path for receiving decontaminating fluid for decontamination of the instrument during a decontamination cycle of the decontaminating apparatus, and
    automatically manipulating the instrument to provide relative movement between two or more relatively movable parts of the instrument during the decontamination cycle, wherein the step of automatically manipulating the instrument includes hydraulically driving the instrument manipulation means by the flow of the decontaminating fluid moving along the fluid flow path of the decontaminating apparatus to put the instrument engaging means in motion during the decontamination cycle.

2. The method of claim 1, wherein the step of automatically manipulating the instrument further comprises:
   transmitting the motion from the instrument engaging means to the instrument to provide the relative movement between the two or more relatively movable parts of the instrument.

3. The method of claim 1, wherein one or more parts of the instrument are stationary during the relative movement between two or more relatively movable parts thereof provided by the step of automatically manipulating the instrument.

4. The method of claim 1, wherein the method further comprises:
   operating a deluge decontamination means of the decontaminating apparatus while performing the step of automatically manipulating the instrument.

5. The method of claim 1, wherein the flow path of the decontaminating apparatus is a flow path along which decontaminating fluid flows for supplying decontaminating fluid to a deluge decontaminating means of the decontaminating apparatus.

6. The method of claim 1, wherein the method further comprises:
   immersing the instrument in the decontaminating fluid during the decontamination cycle, while performing the step of automatically manipulating the instrument.

7. The method of claim 6, wherein the step of automatically manipulating the instrument is performed without applying ultrasonic waves to the decontaminating fluid.

8. The method of claim 1, wherein the decontamination cycle includes supplying a flow of fluid to an interior of the instrument.

9. The method of claim 8, wherein the flow of the decontaminating fluid is a pulsed flow.

10. The method of claim 1, wherein the relative movement provided between the two or more relatively movable parts of the instrument by automatically manipulating the instrument comprises relative movement between parts involved in providing a manipulation of a working portion of the instrument in use.

11. The method of claim 10, wherein the instrument comprises an operating portion for remotely controlling manipulation of the working portion of the instrument in use, wherein the relative movement provided by automatically manipulating the instrument comprises relative movement between parts of the operating portion of the instrument, wherein the operating portion comprises parts that are movable relative to one another to remotely control manipulation of the working portion of the instrument, and the step of automatically manipulating the instrument comprises engaging one or more of the relatively movable parts to transmit motion thereto and provide relative movement between the parts of the operating portion.

12. The method of claim 11, wherein the operating portion provides remote control of manipulation of the working portion of the instrument in use via operation transmission means, wherein the step of automatically manipulating the instrument additionally provides relative motion between parts of operation transmission means.

13. The method of claim 11, wherein the operating portion comprises an operating interface or handle portion comprising the relatively movable parts of the operating portion.

14. The method of claim 13, wherein the operating interface is manually operable or is arranged to be manipulated via a device connected thereto in use.

* * * * *